(12) United States Patent
Sato

(10) Patent No.: US 7,713,198 B2
(45) Date of Patent: May 11, 2010

(54) ULTRASONIC DIAGNOSTIC EQUIPMENT AND METHOD OF CONTROLLING ULTRASONIC DIAGNOSTIC EQUIPMENT

(75) Inventor: Takeshi Sato, Nasu-gun (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 340 days.

(21) Appl. No.: 11/012,333

(22) Filed: Dec. 16, 2004

(65) Prior Publication Data

US 2005/0148875 A1  Jul. 7, 2005

(30) Foreign Application Priority Data

Dec. 17, 2003  (JP)  ............................. 2003-419557

(51) Int. Cl.
*A61B 8/00*  (2006.01)
(52) U.S. Cl. .................. 600/437; 600/453; 600/454; 600/455; 600/468
(58) Field of Classification Search ................ 600/407, 600/408, 437–455; 601/2–4; 604/20–22
See application file for complete search history.

(56) References Cited

U.S. PATENT DOCUMENTS

| | | | |
|---|---|---|---|
| 4,476,874 A * | 10/1984 | Taenzer et al. ............... 600/441 |
| 4,751,847 A | 6/1988 | Katakura et al. |
| 4,759,375 A * | 7/1988 | Namekawa .................. 600/455 |
| 4,884,448 A * | 12/1989 | Ogawa et al. ................. 73/597 |
| 4,911,171 A * | 3/1990 | Uchibori ..................... 600/455 |
| 4,993,417 A | 2/1991 | Seo |
| 5,228,009 A | 7/1993 | Forestieri et al. |
| 5,441,052 A * | 8/1995 | Miyajima ................... 600/455 |

(Continued)

FOREIGN PATENT DOCUMENTS

JP  64-043237  2/1989

(Continued)

OTHER PUBLICATIONS

Zoran B. Banjanin, et al. "Clutter Rejection for Doppler Weather Radars which Use Staggered Pulses", IEEE Transactions on Geoscience and Remote Sensing, vol. 29, No. 4, Jul. 1991, pp. 610-620.

(Continued)

*Primary Examiner*—Long V Le
*Assistant Examiner*—Sanjay Cattungal
(74) *Attorney, Agent, or Firm*—Oblon, Spivak, McClelland, Maier & Neustadt, L.L.P.

(57) ABSTRACT

An ultrasonic Doppler diagnostic equipment according to the present invention is characterized by including a Doppler signal detection device which executes a filtering process for a plurality of reception signals obtained in time series at unequal intervals from a predetermined position within a patient by a transmission/reception device, thereby to detect Doppler signals based on a mobile object; a velocity calculation device which selects Doppler signals obtained at a predetermined time interval, from among the plurality of Doppler signals obtained at the unequal intervals by the Doppler signal detection device, and which calculates a velocity of the mobile object on the basis of the selected Doppler signals; and an image data generation device which generates velocity image data on the basis of the velocity of the mobile object as calculated by the velocity calculation device.

16 Claims, 17 Drawing Sheets

U.S. PATENT DOCUMENTS

| | | | |
|---|---|---|---|
| 5,664,571 A * | 9/1997 | Yamazaki | 600/441 |
| 6,322,510 B1 * | 11/2001 | Kataoka et al. | 600/453 |
| 6,450,961 B1 * | 9/2002 | Shiki et al. | 600/458 |
| 6,669,642 B2 * | 12/2003 | Amemiya et al. | 600/453 |
| 6,673,020 B2 * | 1/2004 | Okada et al. | 600/454 |
| 7,044,913 B2 * | 5/2006 | Shiki | 600/454 |

FOREIGN PATENT DOCUMENTS

| | | |
|---|---|---|
| JP | 3-173551 | 7/1991 |
| JP | 4-197249 | 7/1992 |
| JP | 10-099333 | 4/1998 |

OTHER PUBLICATIONS

W. Wilkening, et al. "Fast, Extended Velocity Range Flow Imaging Based on Nonuniform Sampling Using Adaptive Wall Filtering and Cross Correlation", IEEE Ultrasonics Symposium, 2002, pp. 1457-1460.

U.S. Appl. No. 11/677,280, filed Feb. 21, 2007, Sato.

* cited by examiner

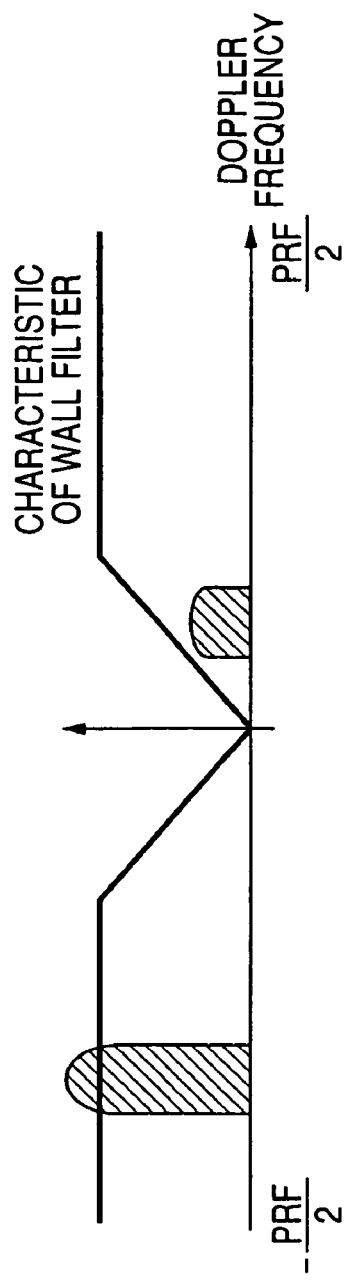
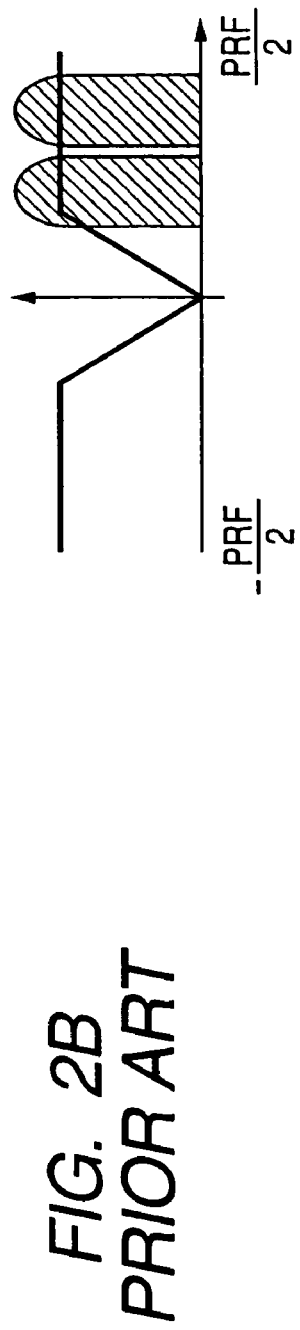
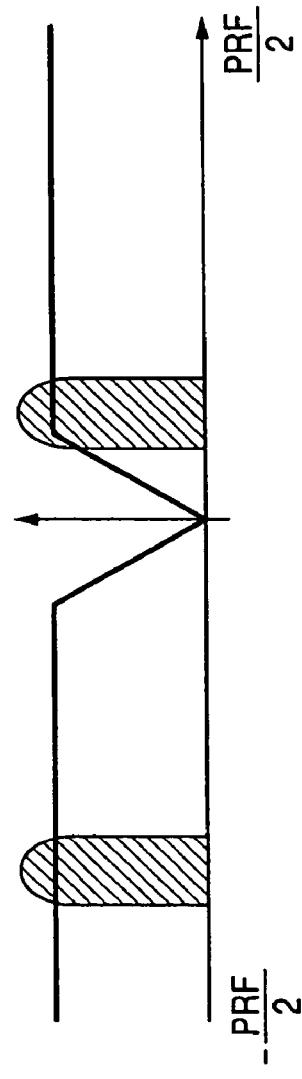
FIG. 2A PRIOR ART
FIG. 2B PRIOR ART
FIG. 2C PRIOR ART

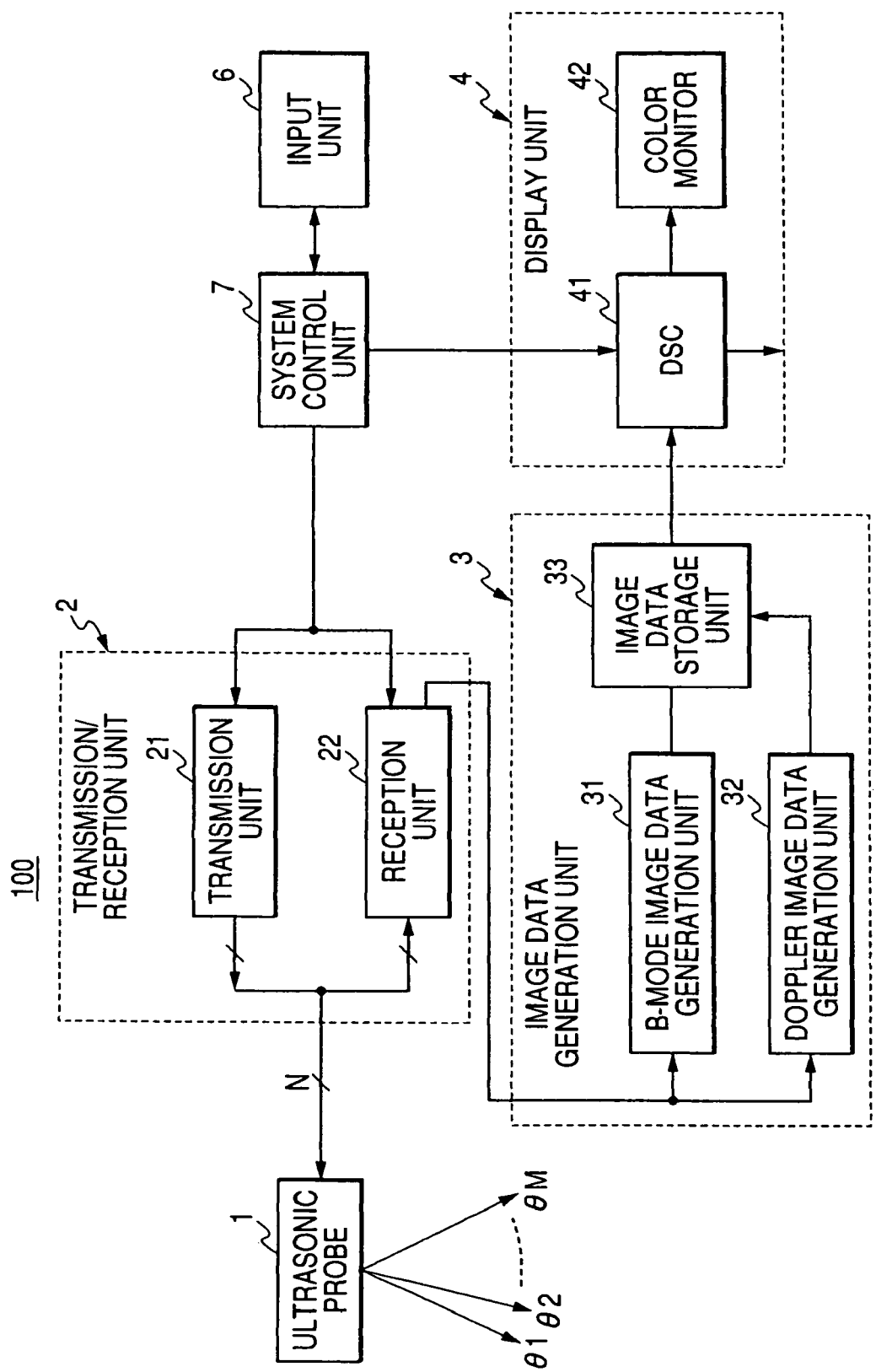

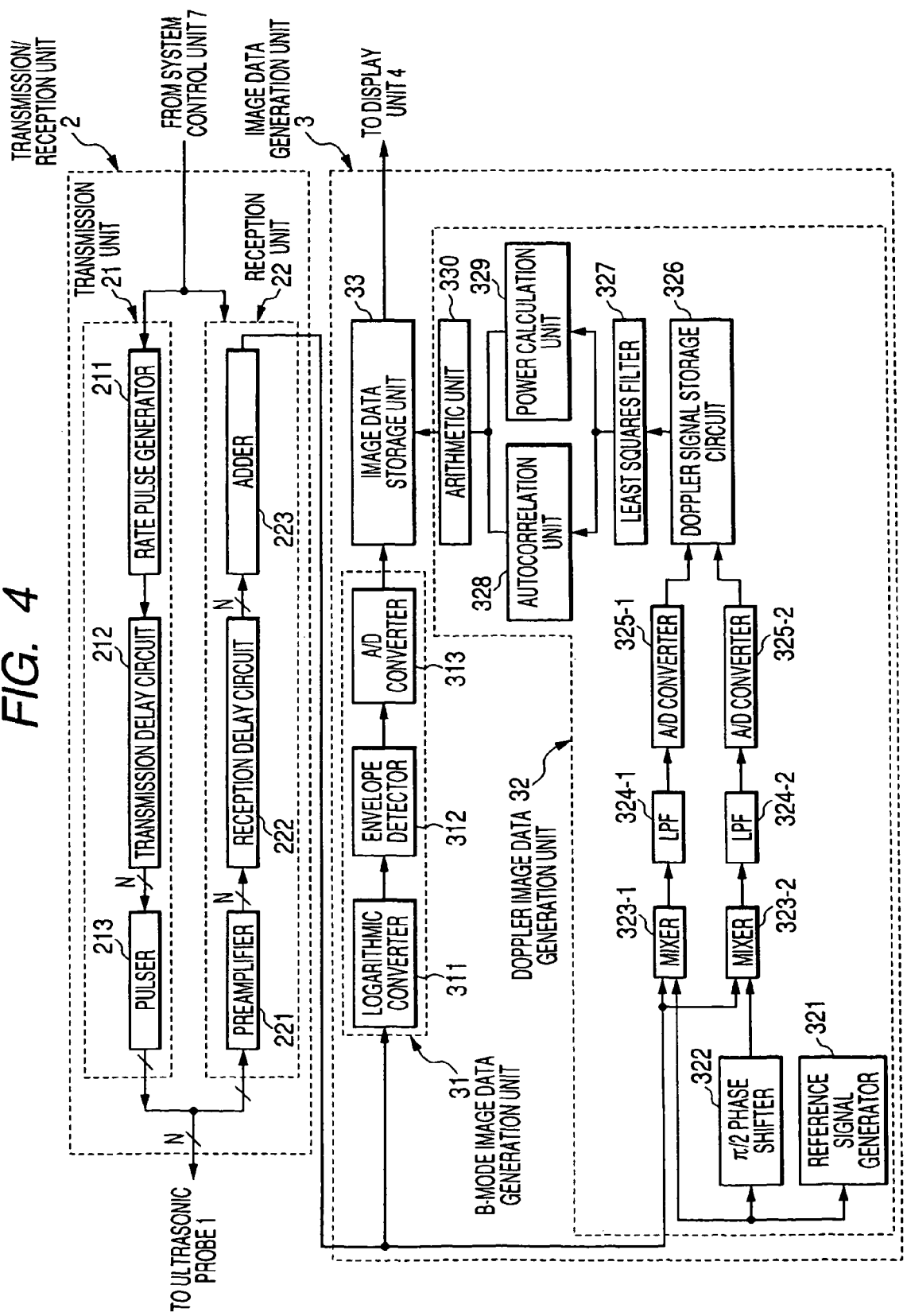

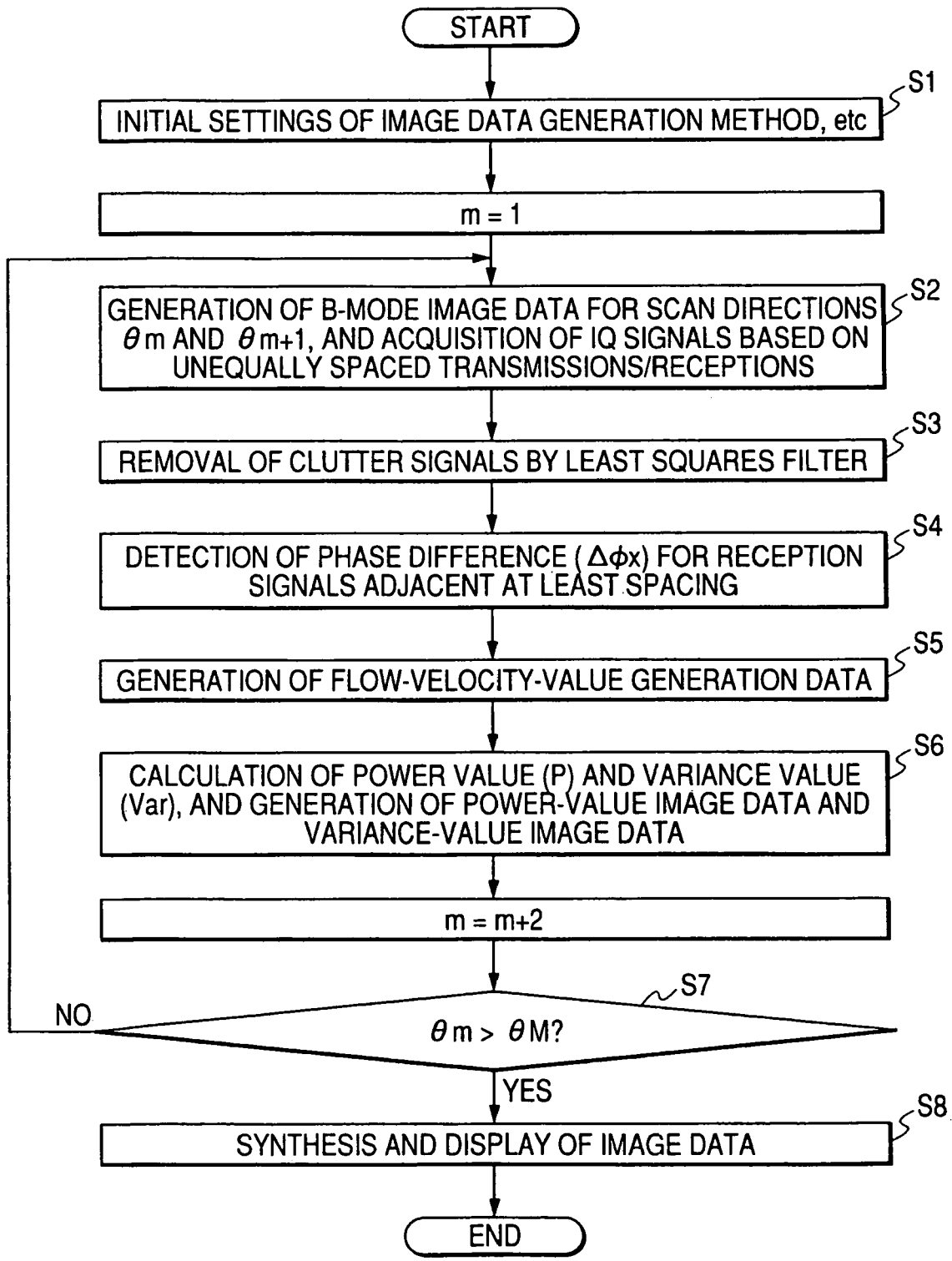

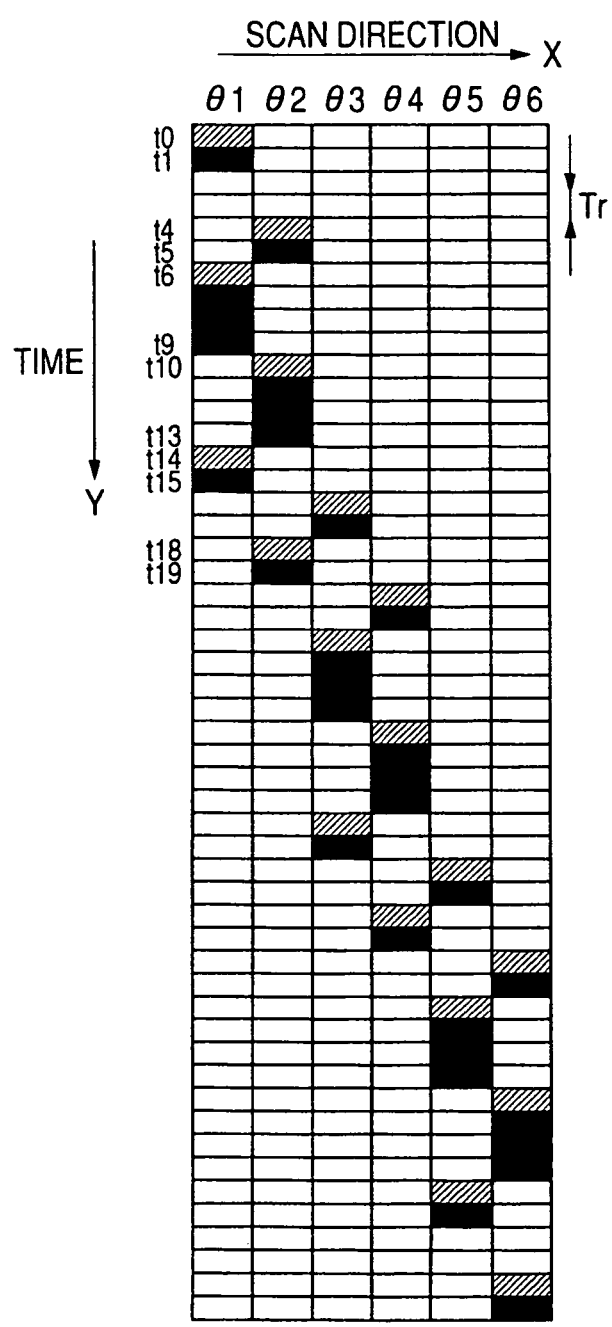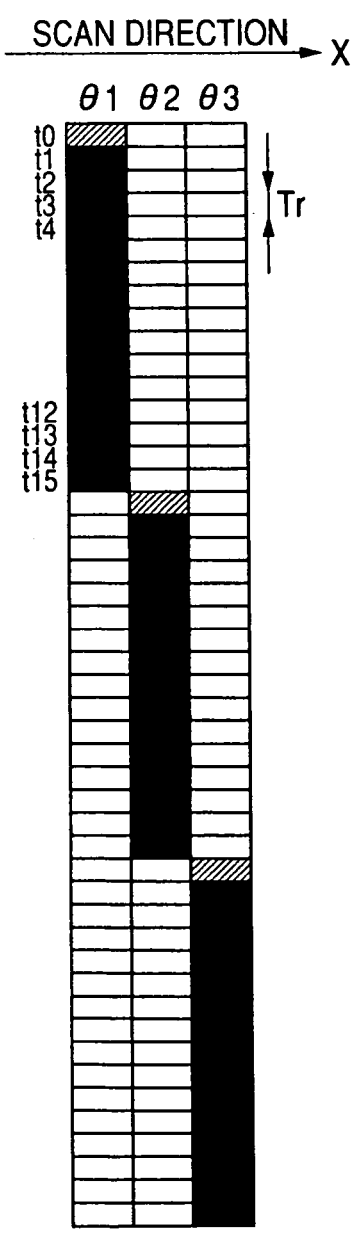
FIG. 11A
FIG. 11B
PRIOR ART

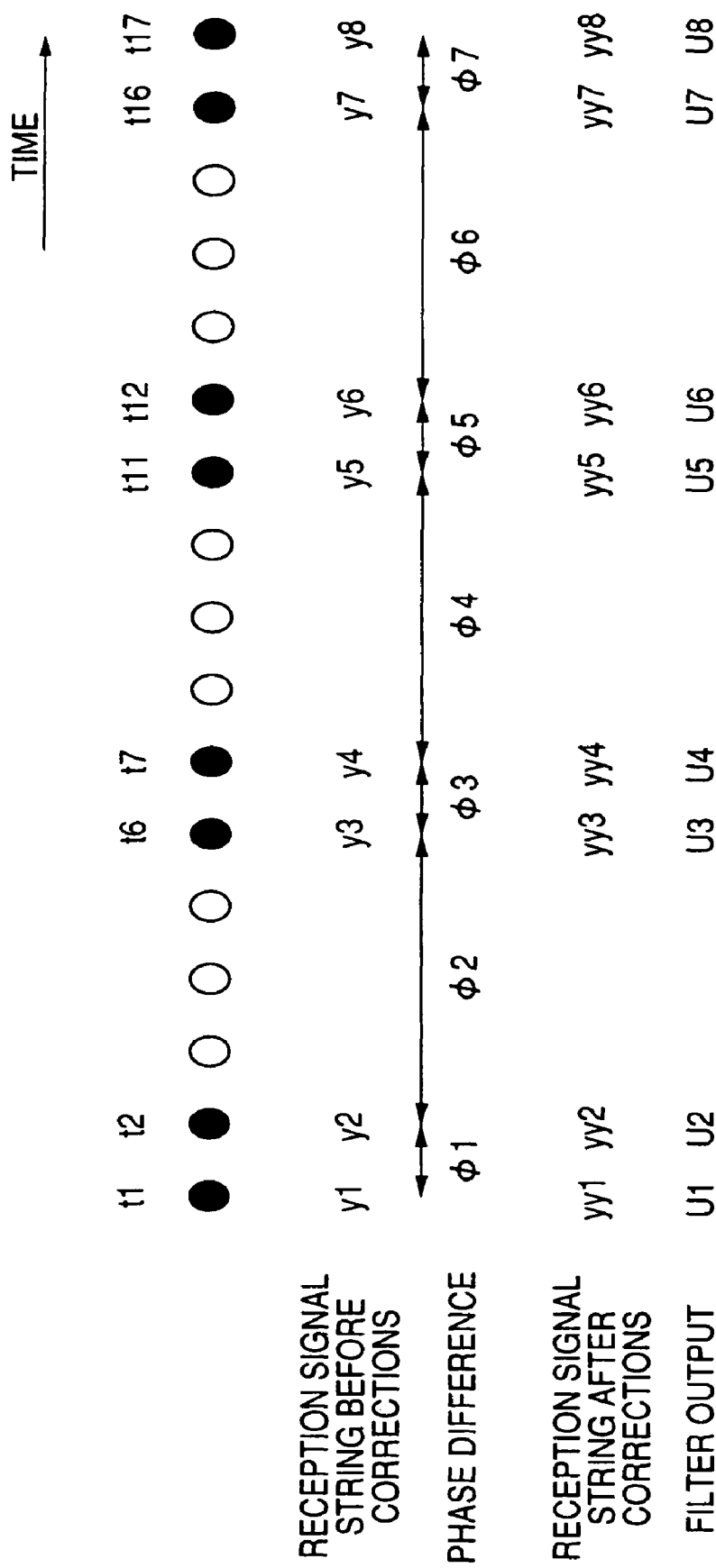

EQUALLY SPACED
INTERLEAVE SCAN
OF 3 STAGES

EQUALLY SPACED
INTERLEAVE SCAN
OF 6 STAGES

UNEQUALLY SPACED
SCAN OF ONE RASTER
IN FIG. 14

ULTRASONIC DIAGNOSTIC EQUIPMENT AND METHOD OF CONTROLLING ULTRASONIC DIAGNOSTIC EQUIPMENT

BACKGROUND OF THE INVENTION

1. Field of the Invention

The present invention relates to an ultrasonic diagnostic equipment wherein color Doppler image data are generated on the basis of ultrasonic Doppler signals obtained from a patient.

2. Description of the Related Art

An ultrasonic diagnostic equipment is such that ultrasonic pulses which have been generated from piezoelectric transducers built in an ultrasonic probe are radiated into a patient, and that ultrasonic reflected waves generated by the difference of the acoustic impedance of a patient tissue are received by the piezoelectric transducers and then displayed on a monitor. Such a diagnostic method is extensively employed for the functional diagnoses and morphological diagnoses of the various internal organs of a living body because a two-dimensional image can be easily observed in real time by the simple operation of merely bringing the ultrasonic probe into touch with the surface of the body.

An ultrasonic diagnostic method which obtains in-vivo information on the basis of reflected waves from a tissue or blood corpuscles within a living body has made rapid progress owing to the great technological developments of two methods; an ultrasonic pulse echo method and an ultrasonic Doppler method. A B-mode image and a color Doppler image which are obtained using the technologies, are indispensable to ultrasonic image diagnoses of today.

A color Doppler method is such that, in a case where a predetermined section within a living body has been scanned with ultrasonic pulses and where a moving reflector such as blood (blood corpuscles) has been irradiated with ultrasounds, imaging is performed by grasping a Doppler frequency shift which is induced in correspondence with the velocity of the reflector (blood flow velocity). The color Doppler method was initially employed for the imaging of a blood flow within the cardiac cavity as exhibits a high blood flow velocity, but nowadays it has become applicable even to the imaging of a very slow blood flow such as the tissue blood flow of an abdominal organ.

In order to enhance a diagnosability with the color Doppler method, a superior measurement precision (low-flow-velocity detectability and high-flow-velocity detectability) is first required, a temporal resolution (real-time responsivity) is secondly done, and a spatial resolution is thirdly done.

Now, the measurement precision being the first requisite will be explained. In a case where a moving reflector is irradiated with ultrasonic pulses and where the moving velocity of the reflector is measured from the Doppler frequency shift of reflected waves from the reflector, it has heretofore been practiced that ultrasound transmissions/receptions to and from the reflector are repeated a plurality of times (L times) at predetermined transmission/reception intervals Tr, and that the moving velocity is measured on the basis of a series of reflected waves obtained within an observation time Tobs (Tobs=Tr·L)

In this case, the detectability for the reflector of low flow velocity (low-flow-velocity detectability: the lower-limit value of measurable flow velocities) as denoted by "Vmin" is determined by the characteristics of a filter, namely, the cutoff frequency and roll-off characteristic of the filter (for example, MTI filter) which is used for detecting Doppler components from within the series of reflected waves obtained by the L times of ultrasonic transmissions/receptions (hereinbelow, simply termed "transmissions/receptions"). The detectability Vmin on this occasion is indicated by the following equation (1) where "fr" (fr=1/Tr) denotes a transmission/reception repetition frequency (rate frequency: pulse repetition frequency (PRF)):

$$V\min \propto \frac{1}{Tobs} = \frac{fr}{L} \quad (1)$$

On the other hand, the upper-limit value of the measurable flow velocities (high-flow-velocity detectability) as denoted by "Vmax" is determined by a Nyquist frequency which is defined by ½ of the transmission/reception repetition frequency (rate frequency) fr, and it is indicated by Equation (2) below. In the equation, "C" denotes an acoustic velocity value within the patient, "fo" denotes the center frequency of received ultrasonic waves, and "ξ" denotes an angle which is defined between an ultrasonic transmission/reception direction and a blood flow direction. Besides, in a case where the Doppler frequency shift has exceeded the Nyquist frequency, an aliasing phenomenon appears in the frequency spectrum of Doppler signals, and hence, the precise measurement of the blood flow velocity becomes impossible.

$$V\max = \frac{C \cdot fr}{4fo \cos \xi} \quad (2)$$

More specifically, in order to enhance the low-flow-velocity detectability Vmin which is one factor of the first requisite in the color Doppler method, the rate frequency fr needs to be set low, or the number of times L of the repetitive transmissions/receptions in a predetermined direction needs to be increased. On the other hand, in order to enhance the high-flow-velocity detectability Vmax which is the other factor of the first requisite, the rate frequency fr must be set high. Since, however, the rate frequency fr has its upper-limit value determined by the field of view, it cannot be heightened still further.

Meanwhile, the real-time responsivity being the second requisite is determined by the number of display images per unit time (frame frequency) "Fn". The frame frequency Fn is indicated by Equation (3) below. In the equation, "M" denotes the total number of scan directions which are necessary for the generation of the data of one color Doppler image, and the number of times L of the transmissions/receptions or the total number M of the scan directions must be set small in order to enhance the real-time responsivity.

$$Fn = \frac{fr}{L \cdot M} = \frac{1}{Tobs \cdot M} \propto \frac{V\min}{M} \quad (3)$$

Further, in order to enhance the spatial resolution being the third requisite, the total number M of the scan directions needs to be increased. That is, the frame frequency Fn (real-time responsivity), the low-flow-velocity detectability Vmin as well as the high-flow-velocity detectability Vmax, and the spatial resolution are in the trade-off relationship, and they are difficult of being simultaneously satisfied. Therefore, importance has been attached to the frame frequency Fn and the high-flow-velocity detectability Vmax in case of blood flow measurements in the region of circulatory organs, and to the frame frequency Fn and the low-flow-velocity detectability Vmin in case of blood flow measurements in abdominal and peripheral organs.

In order to cope with the above problems, a staggered pulse scheme capable of enhancing the high-flow-velocity detectability has been proposed in, for example, JP-A-4-197249 (hereinbelow, termed "Patent Document 1").

The staggered pulse method is a technique wherein transmissions/receptions in a predetermined direction are repeated at, for example, two different transmission/reception intervals T1 and T2 (T2=T1+Ts), and a blood flow velocity is calculated on the basis of the difference value Δθ (Δθ=θ2−θ1) between the phase difference θ1 of reception signals obtained by the transmission/reception at the transmission/reception interval T1 and the phase difference θ2 of reception signals obtained by the transmission/reception at the transmission/reception interval (T1+Ts). An aliasing frequency in this method is determined by the difference Ts of the transmission/reception intervals, and the high-flow-velocity detectability can be bettered by setting the difference Ts to be T1>Ts.

On the other hand, for the blood flow measurements of low flow velocities in the abdominal organs, peripheral blood vessels, etc., a new scan method (hereinbelow, termed "interleave scan method") has been proposed in, for example, JP-A-64-43237 (hereinbelow, termed "Patent Document 2"). FIG. 1 shows a practicable example of the interleave scan method disclosed in Patent Document 2. The upper stage of the figure indicates transmission/reception directions (hereinbelow, termed "scan directions") θ1 through θM in a sector scan, while the lower stage indicates the sequence of transmissions/receptions in the scan directions.

More specifically, with this method, ultrasounds are first transmitted/received in the direction of the scan direction θ1 at a time t1. Subsequently, ultrasounds are transmitted/received in the direction of the scan direction θ2 at a time t2, and in the direction of the scan direction θ3 at a time t3. Further, the transmissions/receptions of ultrasounds are repeated in the Q (Q=3) directions of the scan directions θ1-θ3 again at times t4-t6 and times t7-t9. When the L times (L=3) of transmissions/receptions have been respectively completed at intervals Ts (Ts=3 Tr) in all the directions of the scan directions θ1-θ3 in this way, L times of transmissions/receptions based on the intervals Ts are similarly performed in the directions of the scan directions θ4-θ6, the scan directions θ7-θ9, . . . . According to this method, premising that a limit down to which the cutoff frequency can be lowered with a predetermined attenuation factor satisfied by an identical design method depends upon the observation time "Tobs", the low-flow-velocity detectability "Vmin" becomes the following equation (4).

$$V\min \propto \frac{1}{Tobs \cdot Q} = \frac{fr}{Q \cdot L} = \frac{fs}{L} \quad (Q = 3) \quad (4)$$

Here, "fs" (fs=1/Ts) denotes a transmission/reception repetition frequency for the respective scan directions. That is, according to the practicable example, the transmission/reception repetition frequency fs becomes ⅓ of the rate frequency fr in the case where the interleave scan is not performed. It is accordingly permitted to enhance the low-flow-velocity detectability triple without lowering the frame frequency.

The proposed methods, however, are problematic as stated below. According to the method of Patent Document 1, the phase differences θ1 and θ2 in the Doppler signals obtained by the transmissions/receptions at the different transmission/reception intervals T1 and T2 are respectively evaluated, and the blood flow information is further calculated on the basis of the difference between the phase differences θ1 and θ2. Therefore, the blood flow information to be obtained is liable to become unstable under the influence of noise. In particular, a measurement error which is not negligible develops due to speckle noise ascribable to the interference of ultrasounds.

Further, with this method, the transmissions/receptions at the transmission/reception intervals T1 and T2 are repeated, so that the filter (MTI filter) for extracting the Doppler signals has a blind frequency which is determined by, for example, the sum between the transmission/reception intervals T1 and T2. Accordingly, a Doppler component agreeing with the blind frequency lowers conspicuously to make impossible the calculation of the blood flow information at a high precision.

On the other hand, the method of Patent Document 2 has been proposed for the purpose of measuring the comparatively slow blood flows of the abdomen, etc. Although the low-flow-velocity detectability Vmin is enhanced to 1/Q, also the high-flow-velocity detectability Vmax becomes 1/Q, and the frequence of occurrence of the aliasing phenomenon heightens for fast blood flows. It is therefore impossible to apply this method to the measurements of comparatively fast blood flows.

Concretely, as shown in FIG. 2A, when the region of interest is scanned with a small number of data, for example, 8, the blood flow of low flow velocity is cut by a wall filter and is not displayed by the prior-art method (interleave scan of one stage) in a case where the wall filter has characteristics as shown in the figure.

In contrast, with the method of the interleave scan (of, for example, 2 stages) as disclosed in Patent Document 2, even when the region of interest is scanned with the same number of data, 8 data, the aliasing frequency becomes half. As shown in FIG. 2B, therefore, the characteristics of the wall filter improve, and the blood flow being invisible with the prior-art method becomes visible. However, the problem occurs that a blood flow which goes away is displayed like a blood flow which turns back and comes near.

As shown in FIG. 2C, this problem is solved when the region of interest is scanned with the double number of data, 16 data, by the prior-art method (interleave scan of one stage) At this time, however, the other problem occurs that the frame rate (temporal resolution) lowers.

SUMMARY OF THE INVENTION

The present invention has been made in view of such problems in the prior art, and has for its object to provide an ultrasonic diagnostic equipment which is capable of generating color Doppler image data of superior low-flow-velocity detectability and high-flow-velocity detectability without lowering a frame frequency.

In order to accomplish the object, an ultrasonic diagnostic equipment according to the invention consists in comprising an ultrasonic probe which includes piezoelectric transducers for transmitting/receiving ultrasounds to and from a mobile object within a patient; a transmission/reception device which drives the piezoelectric transducers so as to transmit/receive the ultrasounds at unequal intervals in a predetermined scan direction within the patient; a Doppler signal detection device which executes a filtering process for a plurality of reception signals obtained in time series at the unequal intervals from a predetermined position within the patient by the transmission/reception device, thereby to detect Doppler signals based on the mobile object; a velocity calculation device which selects Doppler signals obtained at a predetermined time interval, from among the plurality of Doppler signals obtained at the unequal intervals by the Doppler signal detection device, and which calculates a velocity of the mobile object on the basis of the selected Doppler signals; and an image data generation device which generates velocity image data on the basis of the velocity of the mobile object as calculated by the velocity calculation device.

Besides, an ultrasonic diagnostic equipment in another aspect of the invention consists in comprising an ultrasonic probe which includes piezoelectric transducers for transmitting/receiving ultrasounds to and from a mobile object within a patient; a transmission/reception device which drives the piezoelectric transducers so as to transmit/receive the ultrasounds at unequal intervals having a first interval and a second interval longer than the first interval, in a first scan direction and a second scan direction within the patient, respectively; a Doppler signal detection device which executes a filtering process for a plurality of reception signals obtained in time series at the unequal intervals from a predetermined position within the patient by the transmission/reception device, thereby to detect Doppler signals based on the mobile-object; a velocity calculation device which selects Doppler signals adjacent at the first interval, from among the plurality of Doppler signals obtained at the unequal intervals by the Doppler signal detection device, and which calculates a velocity of the mobile object on the basis of the selected Doppler signals; a scan control device which performs ultrasonic scans within the patient while the first scan direction and the second scan direction are being successively altered; an image data generation device which generates velocity image data on the basis of the velocities of the mobile object as calculated by the velocity calculation device, in the ultrasonic transmissions/receptions at the unequal intervals in the respective scan directions of the ultrasonic scans; and a display device which displays the generated image data; wherein the ultrasonic transmissions/receptions in the second scan direction are performed at the second interval of the ultrasonic transmissions/receptions in the first scan direction.

An ultrasonic diagnostic equipment in still another aspect of the invention consists in comprising an ultrasonic probe which includes piezoelectric transducers for transmitting/receiving ultrasounds to and from a mobile object within a patient; a transmission/reception device which drives the piezoelectric transducers so as to perform interleave scan at unequal intervals in a predetermined scan direction within the patient; a device which executes a filtering process for a plurality of reception signals obtained in time series at the unequal intervals from a predetermined position within the patient by the transmission/reception device, thereby to measure a velocity of the mobile object; and an image data generation device which generates velocity image data on the basis of the velocity of the mobile object.

On the other hand, a method of controlling an ultrasonic diagnostic equipment according to the invention consists in comprising a transmission/reception step of driving piezoelectric transducers of an ultrasonic probe which includes the piezoelectric transducers for transmitting/receiving ultrasounds to and from a mobile object within a patient, so as to transmit/receive the ultrasounds at unequal intervals in a predetermined scan direction within a patient; a Doppler signal detection step of executing a filtering process for a plurality of reception signals obtained in time series at the unequal intervals from a predetermined position within the patient by the transmission/reception step, thereby to detect Doppler signals based on the mobile object; a velocity calculation step of selecting Doppler signals obtained at a predetermined time interval, from among the plurality of Doppler signals obtained at the unequal intervals by the Doppler signal detection step, and then calculating a velocity of the mobile object on the basis of the selected Doppler signals; and an image data generation step of generating velocity image data on the basis of the velocity of the mobile object as calculated by the velocity calculation step.

Besides, a method of controlling an ultrasonic diagnostic equipment in another aspect of the invention consists in comprising a transmission/reception step of driving piezoelectric transducers of an ultrasonic probe which includes the piezoelectric transducers for transmitting/receiving ultrasounds to and from a mobile object within a patient, so as to transmit/receive the ultrasounds at unequal intervals having a first interval and a second interval longer than the first interval, in a first scan direction and a second scan direction within the patient, respectively; a Doppler signal detection step of executing a filtering process for a plurality of reception signals obtained in time series at the unequal intervals from a predetermined position within the patient by the transmission/reception step, thereby to detect Doppler signals based on the mobile object; a velocity calculation step of selecting Doppler signals adjacent at the first interval, from among the plurality of Doppler signals obtained at the unequal intervals by the Doppler signal detection step, and then calculating a velocity of the mobile object on the basis of the selected Doppler signals; a scan control step of performing ultrasonic scans within the patient while the first scan direction and the second scan direction are being successively altered; an image data generation step of generating velocity image data on the basis of the velocities of the mobile object as calculated by the velocity calculation step, in the ultrasonic transmissions/receptions at the unequal intervals in the respective scan directions of the ultrasonic scans; and a display step of displaying the generated image data; wherein the ultrasonic transmissions/receptions in the second scan direction are performed at the second interval of the ultrasonic transmissions/receptions in the first scan direction.

A method of controlling an ultrasonic diagnostic equipment in still another aspect of the invention consists in comprising a transmission/reception step of driving piezoelectric transducers of an ultrasonic probe which includes the piezoelectric transducers for transmitting/receiving ultrasounds to and from a mobile object within a patient, so as to perform interleave scan at unequal intervals in a predetermined scan direction within the patient; a step of executing a filtering process for a plurality of reception signals obtained in time series at the unequal intervals from a predetermined position within the patient by said transmission/reception step, thereby to measure a velocity of the mobile object; and an image data generation step of generating velocity image data on the basis of the velocity of the mobile object.

According to the invention, the generation of color Doppler image data of superior low-flow-velocity detectability and high-flow-velocity detectability is permitted without-lowering a frame frequency.

BRIEF DESCRIPTION OF THE DRAWINGS

In the accompanying drawings:

FIGS. 2A-2C are diagrams showing the display states of a blood flow in model-like fashion, in which FIG. 2A is a model diagram corresponding to the case-of an interleave scan of one stage and 8 data, FIG. 2B is a model diagram corresponding to the case of an interleave scan of two stages and 8 data, and FIG. 2C is a model diagram corresponding to the case of an interleave scan of one stage and 16 data;

FIG. 3 is a block diagram showing the general configuration of an ultrasonic diagnostic equipment in an embodiment of the present invention;

FIG. 4 is a block diagram showing the configurations of a transmission/reception unit and an image data generation unit in the embodiment;

FIG. 6 is a flow chart showing image data generation steps in-the embodiment;

FIG. 10A is a diagram showing an interleave scan method in a modification to the embodiment, while

FIG. 11A is a diagram showing another interleave scan method in a modification to the embodiment, while FIG. 11B is a diagram showing the sequence of transmissions/receptions in the prior art;

FIG. 12A is a diagram showing the settings of the times of unequally spaced transmissions/receptions in an embodiment and a modification of the invention, while FIG. 12B is a graph showing frequency characteristics which have been obtained by applying a least squares filter to reception signals acquired by the unequally spaced transmissions/receptions;

FIG. 13 is a diagram showing another example of application of the least squares filter in the invention;

DETAILED DESCRIPTION OF THE PREFERRED EMBODIMENTS

Figure 1:
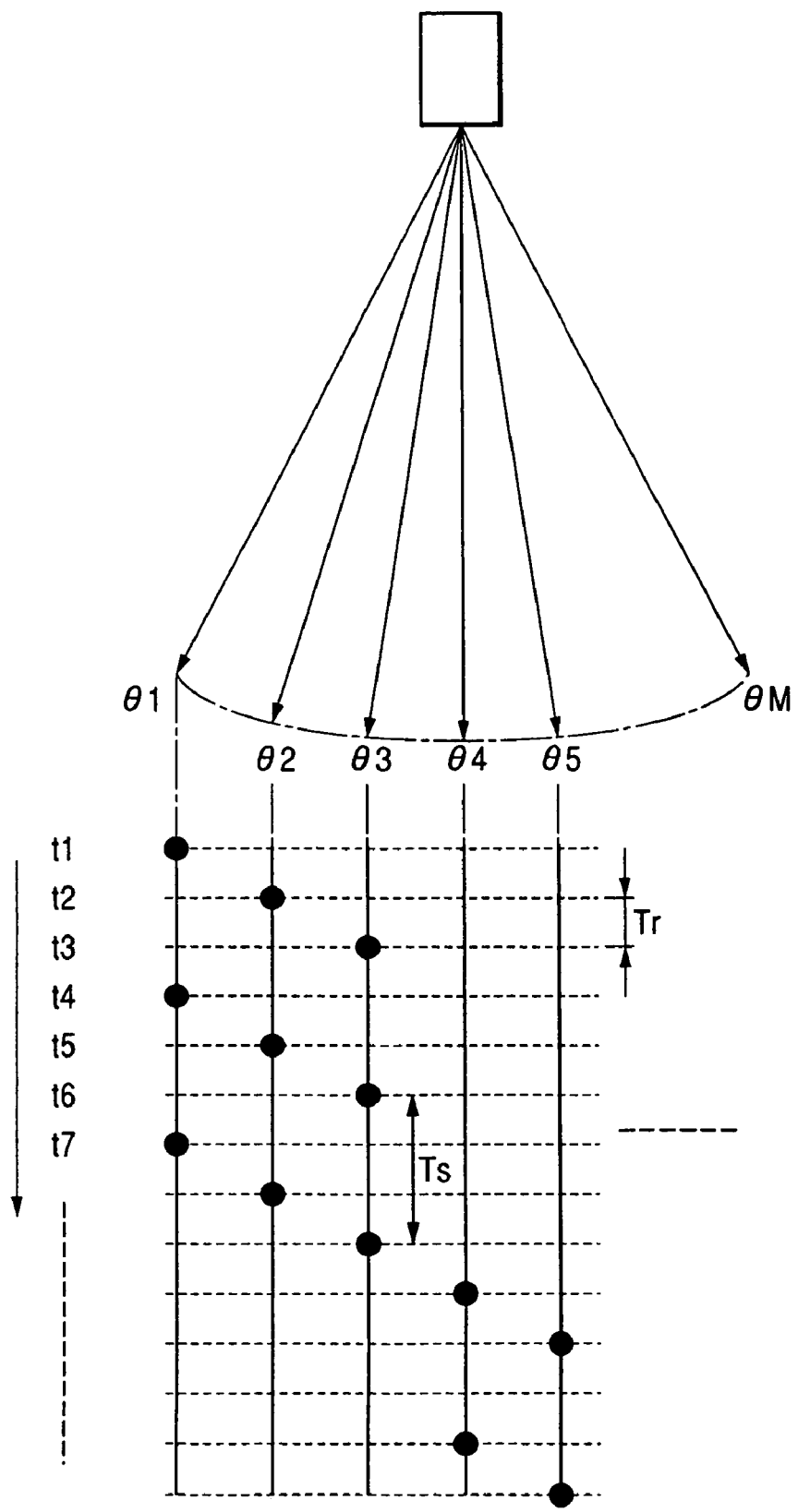
FIG. 1 is a diagram showing an interleave scan method in the prior art.

Now, embodiments of the present invention will be described with reference to the accompanying drawings.

The first characterizing feature of the embodiments consists in that transmissions/receptions spaced unequally (at unequal intervals) are performed in the predetermined direction of a patient, and that a filter which employs the polynomial fitting of the least squares method (hereinbelow, termed "least squares filter") is applied to obtained reception signals, thereby to extract Doppler signals for a blood flow.

Besides, the second characterizing feature of the embodiments consists in that, from among the Doppler signals extracted by the above least squares filter, two Doppler signals which are adjacent at a short transmission/reception interval are selected in one or more places, and that the mean flow velocity value of the blood flow is calculated on the basis of the phase difference between the two adjacent Doppler signals.

Further, the third characterizing feature of the embodiments consists in that, at the long transmission/reception intervals of the transmissions/receptions in the above predetermined direction as set at the unequal intervals, transmissions/receptions are performed in a direction different from the predetermined direction, thereby to execute interleave scan.

(Configuration of Equipment)

Now, the configuration of an ultrasonic diagnostic equipment in an embodiment will be described with reference to FIGS. 3 through 8. Incidentally, FIG. 3 is a block diagram showing the general configuration of the ultrasonic diagnostic equipment in this embodiment, while FIG. 4 is a block diagram showing a transmission/reception unit and an image data generation unit which constitute the ultrasonic diagnostic equipment.

The ultrasonic diagnostic equipment 100 shown in FIG. 3 includes an ultrasonic probe 1 which transmits/receives ultrasounds to and from a patient, a transmission/reception unit 2 which transmits/receives electric signals to and from the ultrasonic probe 1 in order to transmit/receive the ultrasounds in a predetermined scan direction, and an image data generation unit 3 which generates ultrasonic image data on the basis: of reception signals obtained in the scan direction.

Further, the ultrasonic diagnostic equipment 100 includes a display unit 4 which displays the ultrasonic image data generated in the image data generation unit 3, an input unit 6 which inputs acquisition conditions and generation conditions for the image data, various command signals, etc., and a system control unit 7 which generally controls the various units.

The ultrasonic probe 1 transmits/receives the ultrasounds in a state where its front face is held in touch with the surface of the patient, and it has a plurality of (N) piezoelectric transducers arrayed, for example, unidimensionally, at its front end part. Each of the piezoelectric transducers is an electroacoustic transducer, which has the functions of converting an electric pulse (drive signal) into an ultrasonic pulse (transmission ultrasound) in a transmission mode and converting an ultrasonic reflected wave (reception ultrasound) into an electric signal (reception signal) in a reception mode. The ultrasonic probe 1 is constructed to be small in size and light in weight, and it is connected to the transmission/reception unit 2 through a cable of N channels. The ultrasonic probe 1 includes types corresponding to sector scan, linear scan, convex scan, etc., and any of the types is selected optionally in accordance with a part to-be-diagnosed. In the ensuing description, there will be mentioned a case of employing the ultrasonic probe 1 of the type corresponding to the sector scan, but the ultrasonic probe corresponding to another scan such as the convex scan may well be employed.

Next, the transmission/reception unit 2 shown in FIG. 4 includes a transmission unit 21 which generates the drive signal for generating the transmission ultrasounds from the ultrasonic probe 1, and a reception unit 22 which executes phased additions for the reception signals of the plurality of channels as obtained from the piezoelectric transducers of the ultrasonic probe 1. On the other hand, the image data generation unit 3 includes a B-mode image data generation unit 31 which subjects the reception signals after the phased additions, to signal processing for generating B-mode image data, and a Doppler image data generation unit 32 which detects IQ signals from the reception signals after the phased additions, and which executes signal processing for generating color Doppler image data, on the basis of the IQ signals.

The transmission unit 21 of the transmission/reception unit 2 includes a rate pulse generator 211, a transmission delay circuit 212, and a pulser 213. The rate pulse generator 211 feeds the transmission delay circuit 212 with rate pulses that determine the transmission/reception intervals in the case of transmitting/receiving the ultrasounds to and from the patient in unequal spaced fashion.

On the other hand, the transmission delay circuit 212 is constructed of independent delay circuits in the same number (N channels) as that of the piezoelectric transducers which are used for the transmissions in the ultrasonic probe 1. This transmission delay circuit 212 endows the rate pulses with focusing delay times for converging the ultrasounds to predetermined depths in order to attain a fine beam width in the transmissions, and with deflecting delay times for transmitting the ultrasounds in predetermined directions, whereupon it feeds the resulting rate pulses to the pulser 213.

The pulser 213 includes independent drive circuits in the same number (N channels) as that of the piezoelectric transducers which are used for the transmissions. This pulser 213 drives the N piezoelectric transducers built in the ultrasonic probe 1, so as to generate the drive pulses for radiating the transmission ultrasounds into the patient.

On the other hand, the reception unit 22 includes a preamplifier 221, a reception delay circuit 222 and an adder 223 each of which is of N channels. The preamplifier 221 amplifies minute reception signals converted into electric signals by the piezoelectric transducers, thereby to ensure a satisfactory S/N ratio. Besides, the reception delay circuit 222 endows the outputs of the preamplifier 221 with converging delay times for focusing the reception ultrasounds from predetermined depths in order to attain a fine reception beam width, and with deflecting delay times for setting reception directivities for the ultrasounds from predetermined depths. Thereafter, the outputs of the reception delay circuit 222 are sent to the adder 223, and the reception signals of the N channels from the reception delay circuit 222 are added and synthesized in this adder 223.

Next, the image data generation unit 3 includes the B-mode image data generation unit 31, the Doppler image data generation unit 32, and an image data storage unit 33. The B-mode image data generation unit 31 has a logarithmic converter 311, an envelope detector 312 and an A/D converter 313. The input signal amplitude of the B-mode data generation unit 31 is logarithmically converted in the logarithmic converter 311 so as to relatively emphasize weak signal components. Besides, the envelope detector 312 performs envelope detection for the reception signal subjected to the logarithmic conversion, thereby to remove ultrasonic frequency components. Further, the A/D converter 313 subjects the output signal of the envelope detector 312 to A/D conversion, thereby to generate B-mode image data. Incidentally, the logarithmic converter 311 and the envelope detector 312 may well be arranged in the reverse order.

On the other hand, the Doppler image data generation unit 32 includes a reference signal generator 321, a π/2 phase shifter 322, mixers 323-1 and 323-2, LPFs (low-pass filters) 324-1 and 324-2, A/D converters 325-1 and 325-2, and a Doppler signal storage circuit 326. Thus, the generation unit 32 performs orthogonal phase detection for the reception signal fed from the transmission/reception unit 2, thereby to generate the IQ signals.

More specifically, the input signal of the Doppler image data generation unit 32 as fed from the reception unit 22 is inputted to the first input terminals of the mixers 323-1 and 323-2. On the other hand, the continuous wave output of the reference signal generator 321, which has a frequency substantially equal to the center frequency of the input signal and which is synchronous to the rate pulse of the rate pulse generator 211, is directly fed to the second input terminal of the mixer 323-1, and it has its phase shifted 90 degrees in the π/2 phase shifter 322 and is then fed to the second input terminal of the mixer 323-2. Besides, the outputs of the mixers 323-1 and 323-2 are respectively fed to the LPFs 324-1 and 324-2, thereby to detect only the components of the difference between the output signal frequency of the reception unit 22 and that of the reference signal generator 321.

Subsequently, the A/D converters 325-1 and 325-2 samples the output signals of the respective LPFs 324-1 and 324-2, that is, the IQ signals obtained by the orthogonal phase detection, at a predetermined sampling period, and they convert the sampled signals into digital signals.

That is, the Doppler image data generation unit 32 executes the orthogonal phase detections for the reception signals obtained by the transmissions/receptions which are performed at the unequal intervals a plurality of times (Lx times) for the predetermined scan direction, and it successively saves obtained I components (real components of complex signals) and Q components (imaginary components of the complex signals) in the Doppler signal storage circuit 326.

Further, the Doppler image data generation unit 32 includes a least squares filter 327, an autocorrelation unit 328, a power calculation unit 329 and an arithmetic unit 330 which serve to generate color Doppler image data for the obtained IQ signals. Besides, the generation unit 32 extracts the IQ signals in the number Lx, at an identical position (depth) in the predetermined scan direction as are saved in the Doppler signal storage circuit 326, and it detects the IQ signals (Doppler signals) based on a blood flow, from among the extracted IQ signals. Subsequently, the generation unit 32 selects the IQ signals adjacent at, for example, the least rate interval, from among the extracted IQ signals in the number Lx, and it calculates the mean flow velocity value of the blood flow (hereinbelow, termed "flow velocity value") on the basis of the phase difference between the selected IQ signals.

The least squares filter 327 subjects the IQ signals once saved in the Doppler signal storage circuit 326, to the removal of Doppler signals (clutter signals) which are ascribable to reflected signals from stationary reflectors such as internal organs, the respiratory movements or pulsatory movements of internal organs, etc. More specifically, the least squares filter 327 executes polynomial least squares fitting for the I signals and Q signals in the number Lx as have been obtained from the same part in the predetermined scan direction. The IQ signals extracted by the curve fitting are constituted by the clutter components, and the Doppler components based on the blood flow have been removed from these IQ signals. Accordingly, the Doppler components based on the blood flow can be calculated by subtracting the IQ signals after the curve fitting, from the IQ signals before the curve fitting.

Figure 5A:
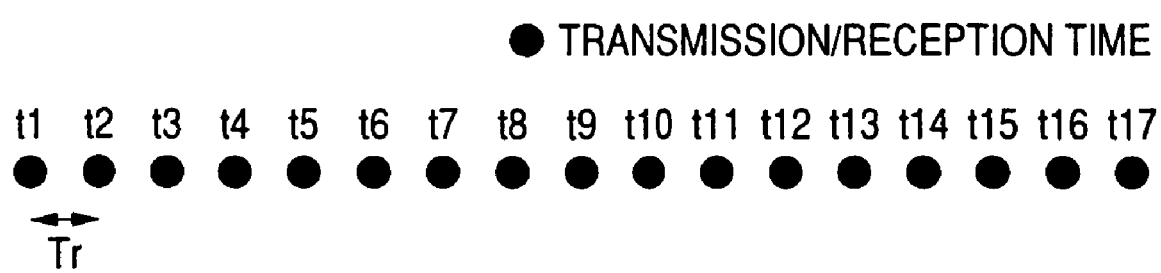
FIG. 5 is a diagram showing transmission/reception timings in unequally spaced transmissions/receptions in the embodiment.
Figure 5B:
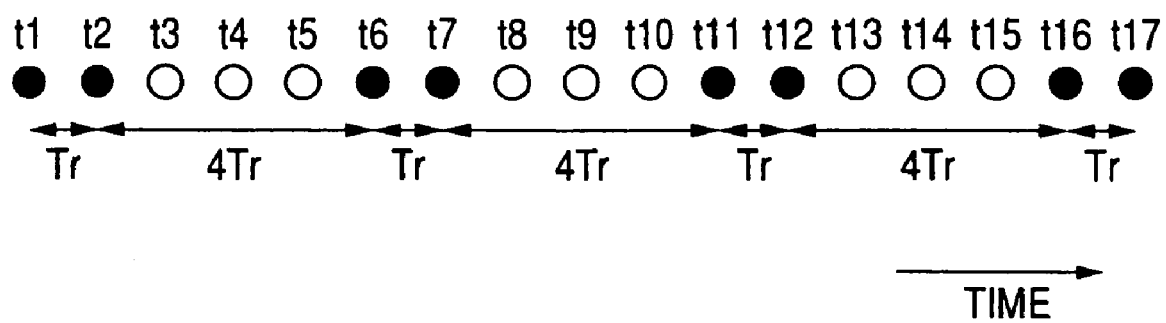

FIG. 5 is for explaining the timings of the ultrasonic transmissions/receptions which proceed at unequal intervals or unequally spaced fashion. Part (a) in FIG. 5 shows the prior-art transmission/reception method in which 17 times of transmissions/receptions based on equal intervals Tr are performed at times t1 through t17. Besides, part (b) in FIG. 5 shows the transmission/reception method of this embodiment in which the transmissions/receptions are performed at the times t1, t2, t6, t7, t11, t12, t16 and t17 among the above times t1 through t17. Incidentally, although any of the unequal intervals of the transmissions/receptions in this embodiment can be set at will, the unequally spaced transmissions/receptions in which the transmission/reception intervals are set at integral times the transmission/reception interval Tr in the prior-art transmission/reception method will be stated for the brevity of description.

Accordingly, the IQ signals which are outputted from the Doppler signal storage circuit 326 of the image data generation unit 3 are constituted by the intervals Tr and the intervals 4 Tr as shown at the part (b) in FIG. 5, and such IQ signals unequally spaced are subjected to the polynomial least squares fitting. More specifically, the fitting becomes the problem that, in a case where the input signal vector [X] of the input signals fed to the least squares filter 327 is denoted by $[X]=[1, 2, 6, 7, 11, 12, 16, 17]^T$ and where the signal vector [Y] after the least squares fitting is denoted by $[Y]=[y1, y2, y3, y4, y5, y6, y7, y8]^T$, [X] is found for a polynomial matrix [A] indicated by [Y]=[A] [X] . Here, $[\ ]^T$ represents a transposed matrix. In this case, if [A] is regular, [X] can be calculated by an inverse matrix. However, in a case where the rank of the polynomial matrix [A] is smaller than the number of rows of the input signal vector [X] as in quadratic polynomial fitting, the least squares solution [X'] of the input signal vector [X] is to be obtained.

That is, the least squares solution can be obtained in accordance with a polynomial matrix [B] which is indicated by [X']=[B][Y]. On this occasion, the polynomial matrix [B] is indicated by a pseudo-inverse matrix $[B]=([A]^T[A])^{-1}[A]^T$. Here, $[\ ]^{-1}$ represents the inverse matrix. A blood flow signal [U] which is the output signal of the least squares filter 327, is obtained by a matrix computation [U]=[W][Y] which uses a filter matrix [W] and the output signal vector [Y]. Here, [W]=[I]-[A][B] holds, and [I] represents a unit matrix.

By the way, in the unequally spaced transmissions/receptions shown in FIG. 5, the above polynomial matrix [A] in the case of approximating the clutter signals by a quadratic polynomial is indicated by the following equation (5):

$$[A] = \begin{pmatrix} 1^0 & 2^0 & 6^0 & 7^0 & 11^0 & 12^0 & 16^0 & 17^0 \\ 1^1 & 2^1 & 6^1 & 7^1 & 11^1 & 12^1 & 16^1 & 17^1 \\ 1^2 & 2^2 & 6^2 & 7^2 & 11^2 & 12^2 & 16^2 & 17^2 \end{pmatrix} = \begin{pmatrix} 1 & 1 & 1 & 1 & 1 & 1 & 1 & 1 \\ 1 & 2 & 6 & 7 & 11 & 12 & 16 & 17 \\ 1 & 4 & 36 & 49 & 121 & 144 & 256 & 289 \end{pmatrix} \quad (5)$$

The filter matrix [W] in the case of the approximation by the quadratic polynomial is given by the following equation (6):

$$[W] = [I] - [A][B] = [I] - [A]([A]^T[A])^{-1}[A]^T = \quad (6)$$

[0.4198 − 0.4556 − 0.0810 − 0.0183 0.1087 0.1095 −

0.0111 − 0.0722 − 0.4556 0.6222 −

0.1333 − 0.0889 0.0222 0.0333 0.0111 −

0.0111 − 0.0810 − 0.1333 0.7429 −

0.2667 − 0.2190 − 0.1857 0.0333 0.1095 −

0.0183 − 0.0889 − 0.2667 0.7151 − 0.2532 −

0.2190 0.0222 0.1087 0.1087 0.0222 −

0.2190 − 0.2532 0.7151 − 0.2667 −

0.0889 − 0.0183 0.1095 0.0333 − 0.1857 −

0.2190 − 0.2667 0.7429 − 0.1333 −

0.0810 − 0.0111 0.0111 0.0333 0.0222 −

0.0889 − 0.1333 0.6222 − 0.4556 −

0.0722 − 0.0111 0.1095 0.1087 −

0.0183 − 0.0810 − 0.4556 0.4198]

Next, the autocorrelation unit 328 selects the IQ signals adjacent at, for example, the least transmission/reception interval, from among the IQ signals obtained by extracting only the Doppler signals of the blood flow by the least squares filter 327, and it detects a phase difference by the autocorrelation processing of the selected IQ signals. More specifically, in the case of the transmission/reception method shown at the part (b) in FIG. 5, the phase difference between the two IQ signals adjacent at the transmission/reception interval Tr. However, in the series of transmissions/receptions which have been performed at the times t1, t2, t6, t7, t11, t12, t16 and t17 in the predetermined direction, the IQ signals obtained at the initial times t1 and t2 and the terminal times t16 and t17 are the data of end parts and accordingly have large velocity estimation errors. Therefore, such phase differences should desirably be detected using the IQ signals except the IQ signals of the large errors.

Here, the IQ signals "Ui" obtained at the times t6, t7, t11 and t12 can be represented by Equation (7) below in which "ai" denotes the I components, and "bi" (i=6, 7, 11, 12) denotes the Q components. Besides, "j" indicates an imaginary unit.

$$U6 = a6 + jb6 = K6 \, \exp(j\phi 6) \quad (7)$$
$$U7 = a7 + jb7 = K7 \, \exp(j\phi 7)$$
$$U11 = a11 + jb11 = K11 \, \exp(j\phi 11)$$
$$U12 = a12 + jb12 = K12 \, \exp(j\phi 12)$$
$$Ki = \sqrt{ai^2 + bi^2} \quad \phi i = \tan^{-1}\frac{bi}{ai} \, L$$

Subsequently, as indicated by Equation (8) below, the autocorrelation unit 328 calculates the mean value "Ux" of the product between the complex conjugate of the IQ signal U6 and the IQ signal U7 and the product between the complex conjugate of the IQ signal U11 and the IQ signal U12, and the arithmetic unit 330 calculates the phase difference "Δφx" in terms of the argument of the mean value Ux.

$$Ux = \frac{conj(U6) \cdot U7 + conj(U11) \cdot U12}{2} \quad (8)$$
$$= \frac{K6 \cdot K7\exp(j(\phi 7 - \phi 6)) + K11 \cdot K12\exp\{j(\phi 12 - \phi 11)\}}{2}$$
$$= Kx \cdot \exp(j\Delta\phi x)$$
$$\Delta\phi x = \tan^{-1}\frac{imag(Ux)}{real(Ux)}$$

On this occasion, the mean flow velocity value in which the phase difference Δφx (−π through π) has π held in correspondence with a turn-back velocity is indicated in the above flow-velocity-value image data.

Subsequently, as indicated in Equation (9) below, the power calculation unit 329 calculates a power value "P" by taking the sum-square mean value of the power levels of the IQ signals U1, U2, U6, U7, U11, U12, U16 and U17 at the times t1, t2, t6, t7, t11, t12, t16 and t17 as obtained in the least squares filter 327, and the arithmetic unit 330 calculates a variance value "Var" by using the power value P and the mean value Ux in the above equation (8).

$$P = \frac{|U1|^2+|U2|^2+|U6|^2+|U7|^2+|U11|^2+|U12|^2+|U16|^2+|U17|^2}{8}$$

$$\mathrm{Var} = 1 - 2\frac{|conj(U6)\cdot U7 + conj(U11)\cdot U12|}{|U6|^2+|U7|^2+|U11|^2+|U12|^2}$$

(9)

By the way, in the calculation of the power value P, the end parts stated above are little influential, and hence, all the IQ signals fed from the least squares filter 327 should desirably be used as indicated in the above equation (9).

Meanwhile, the image data storage unit 33 successively saves the B-mode image data fed from the A/D converter 313 of the B-mode image data generation unit 31, and the flow-velocity-value image data, power-value image data and variance-value image data fed from the arithmetic unit 330 of the Doppler image data generation unit 32, so as to generate two-dimensional B-mode image data, flow-velocity-value image data, power-value image data and variance-value image data.

Referring back to FIG. 3, the display unit 4 includes a DSC (Digital Scan Converter) 41 and a color monitor 42. The DSC 41 includes a CPU (Central Processing Unit) and a storage circuit, neither of which is shown. This DSC 41 generates displaying image data by synthesizing the B-mode image data and flow-velocity-value image data, or the B-mode image data and power-value image data which are fed from the image data storage unit 33 of the image data generation unit 3. Besides, the color monitor 42 displays the displaying image data generated in the DSC 41. Incidentally, the displaying image data may well be generated in such a way that flow-velocity-value/variance-value image data, in which the flow velocity value and the variance value are synthesized and which replace the flow-velocity-value image data, are synthesized with the B-mode image data.

In this case, the DSC 41 generates the displaying image data of single image in which the color Doppler image data, such as flow-velocity-value image data or power-value image data, are superposed on the B-mode image data forming a background image. Besides, the color monitor 42 color-displays the color Doppler image data with the black-and-white B-mode image data as a background.

By the way, in the above display, the power value obtained in the arithmetic unit 330 is displayed as the power-value image data directly or after logarithmic conversion, but each individual pixel of the flow-velocity-value image data or the flow-velocity-value/variance-value image data is displayed only in a case where the pixel value (power value) of the power-value image data corresponding to the pertinent pixel is, at least, equal to a preset threshold value.

Next, the input unit 6 includes input devices such as a keyboard and a track ball or mouse, and a display panel on an input panel. It is used for inputting patient information, a part to-be-diagnosed, an image data acquisition mode, an image data generation method, an image data display method, and various command signals. By way of example, with the input unit 6, an ultrasonic scan method and a display mode are selected, and transmission/reception intervals and conditions concerning interleave scans and the least squares filter 327 are set.

Besides, the system control unit 7 includes a CPU and a storage circuit, not shown, and it generally performs the controls of the various units of the ultrasonic diagnostic equipment 100 and the control of the whole system. In particular, the system control unit 7 functions so that the ultrasonic scan method and display mode, and the transmission/reception intervals and conditions concerning interleave scans and the least squares filter 327 as are set in the input unit 6 may be once saved in the storage circuit and thereafter fed to the corresponding units.

(Generation Steps of Procedure for Image Data)

Next, generation steps of procedure for image data in an embodiment of the present invention as applies an interleave scan method will be described with reference to FIGS. 3 through 9. Incidentally, FIG. 6 is a flow chart showing the generation steps of procedure for image data, and FIG. 7 shows a practicable example of the interleave scan method.

Figure 7:
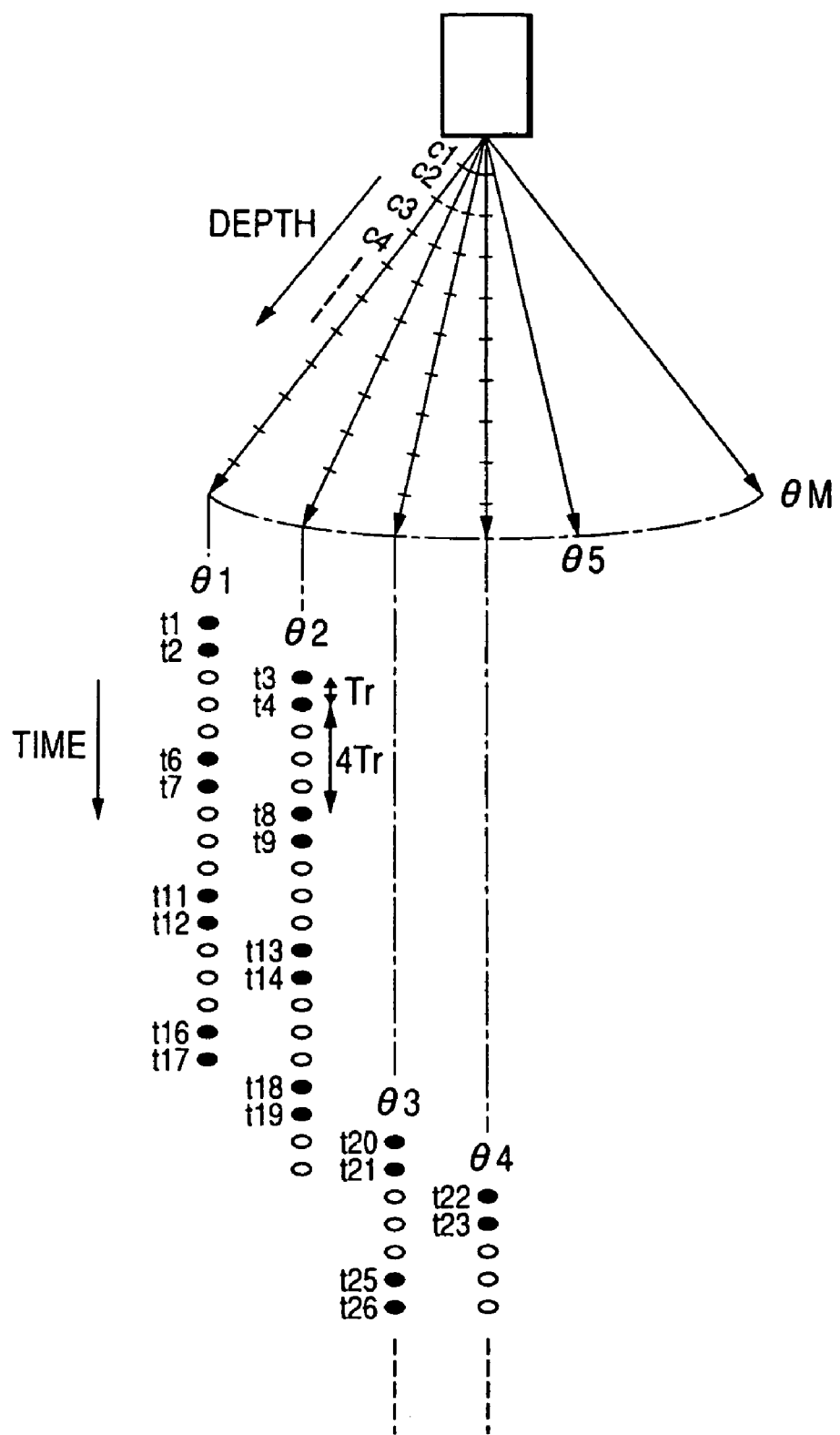
FIG. 7 is a diagram showing a practicable example of an interleave scan method in the embodiment.

FIG. 7 indicates scan directions θ1 through θM in sector scan, and the sequence of transmissions/receptions for the scan directions θ1 through θ4. More specifically, ultrasounds are transmitted/received in the scan direction θ1 at, for example, times t1, t2, t6, t7, t11, t12, t16 and t17 in the same manner as in FIG. 5. Besides, ultrasounds are transmitted/received in the scan direction θ2 at times t3, t4, t8, t9, t13, t14, t18 and t19 at which the transmissions/receptions for the scan direction θ1 do not proceed.

When the interleave scan for the scan directions θ1 and θ2 have ended, interleave scans are successively performed for the scan directions θ3 and θ4, θ5 and θ6, . . . in accordance with similar steps of procedure. By the way, also in this case, adjacent transmission/reception intervals are set at integral times a predetermined interval Tr. By way of example, the intervals of the times t1 and t2, t3 and t4, t6 and t7, . . . are set at Tr, and those of the times t2 and t6, t4 and t8, t7 and t11, . . . are set at 4 Tr. Generation steps of procedure for color Doppler image data in the case of applying such an interleave scan method will be described below.

Before acquiring image data, an operator gives initial settings concerning patient information, a part to-be-diagnosed, an image data acquisition mode, an image data generation method, an image data display method, etc. through the input unit 6, so as to save the set information items in the storage circuit of the system control unit 7. In this embodiment, a mode for acquiring the B-mode image data and the color Doppler image data by the sector scan is set as the image data acquisition mode. Besides, the interleave scan method of two stages (two directions) is selected as the image data generation method (step S1 in FIG. 6).

When the initial settings stated above have ended, the operator fixes the distal end (ultrasonic transmission/reception face) of the ultrasonic probe 1 to a predetermined position on the bodily surface of a patient and then starts acquiring the image data. In transmitting/receiving ultrasounds in the scan direction θ1 at the time t1, the rate pulse generator 211 in FIG. 4 feeds the transmission delay circuit 212 with a rate pulse which determines the radiation timing of the transmission ultrasounds to be radiated into the body of the patient, in synchronism with a control signal from the system control unit 7.

The transmission delay circuit 212 endows the rate pulse with delay times for converging the ultrasounds to predetermined depths in order to attain a fine beam width in the transmissions, and with delay times for transmitting the ultrasounds in the scan direction θ1, whereupon it feeds the resulting rate pulses to the pulser 213. Subsequently, the pulser 213 drives the piezoelectric transducers built in the ultrasonic probe 1, by using piezoelectric-transducer drive pulses which are generated by the feed of the delayed rate pulses, so as to radiate ultrasonic pulses (transmission ultrasounds) into the patient.

Some of the transmission ultrasounds radiated into the patient are reflected from a tissue or the interface between internal organs of different acoustic impedances. Also, the transmission ultrasounds are sometimes reflected by mobile reflectors such as the cardiac wall and blood corpuscles. In such a case, the ultrasonic frequency of the transmission ultrasounds undergoes a Doppler shift.

Ultrasonic reflected waves (reception ultrasounds) reflected from the patient tissue or blood corpuscles are received by the piezoelectric transducers of the ultrasonic probe 1, and are converted into electric signals (reception signals). The reception signals are amplified by the preamplifier 221 of N independent channels in the reception unit 22 of the transmission/reception unit 2, and are fed to the reception delay circuit 222 of N channels.

The reception delay circuit 222 endows the reception signals with focusing delay times for converging the ultrasounds received from the predetermined depths, and deflecting delay times for receiving the ultrasounds with an intense reception directivity in the first scan direction (θ1), whereupon it feeds the resulting reception signals to the adder 223. Besides, the adder 223 adds and synthesizes the reception signals of N channels outputted from the reception delay circuit 222, into a single reception signal, whereupon it feeds the single reception signal to the B-mode image data generation unit 31 and Doppler image data generation unit 32 of the image data generation unit 3.

The output signal of the adder 223 as fed to the B-mode image data generation unit 31 is subjected to logarithmic conversion, envelope detection and A/D conversion, whereupon the resulting data are saved in a B-mode image data storage area within the image data storage unit 33.

Subsequently, ultrasounds are transmitted/received for the scan direction θ2 in accordance with the same procedure, and B-mode image data obtained are saved in the B-mode image data storage area of the image data storage unit 33.

Meanwhile, in generating the color Doppler image data, a plurality of times of transmissions/receptions are performed for each of the scan directions θ1 and θ2 in accordance with the same procedure as described above, in order to find the Doppler shift of reception signals, and flow-velocity-value image data, variance-value image data and power-value image data are generated on the basis of the reception signals obtained on this occasion.

More specifically, when B-mode image data in the above scan directions θ1 and θ2 have been acquired and saved, the system control unit 7 feeds the transmission/reception unit 2 and the image data generation unit 3 with a start command signal for generating the color Doppler image data in the scan directions θ1 and θ2. Besides, as in the case of the B-mode image data, the transmission/reception unit 2 first transmits/receives ultrasounds in the scan direction θ1 and feeds the Doppler image data generation unit 32 with the reception signals obtained.

The output signal of the reception unit 22 as fed to the Doppler image data generation unit 32 in FIG. 4 is subjected to orthogonal phase detection by the mixers 323-1, 323-2 and LPFs 324-1, 324-2, thereby to be converted into an IQ signal of 2 channels. Besides, the I component and Q component of the IQ signal are respectively converted by the A/D converters 325-1, 325-2 into digital signals, which are thereafter saved in the Doppler signal storage circuit 326. Subsequently, also at the time t=t2, ultrasounds are transmitted/received in the scan direction θ1 in accordance with the same procedure, whereupon an IQ signal obtained is saved in the Doppler signal storage circuit 326.

Subsequently, at the times t3 and t4, the transmission/reception unit 2 transmits/receives ultrasounds in the scan direction θ2 in accordance with control signals from the system control unit 7, whereupon IQ signals obtained are saved in the Doppler signal storage circuit 326.

Thenceforth, transmissions/receptions are similarly performed for the scan direction θ1 at the times t6 and t7, t11 and t12, and t16 and t17, and for the scan direction θ2 at the times t8 and t9, t13 and t14, and t18 and t19. IQ signals obtained on these occasions are also saved in the Doppler signal storage circuit 326.

When the IQ signals obtained by the Lx times (eight times) of transmissions/receptions for the scan directions θ1 and θ2 have been saved, transmissions/receptions are also performed for the scan directions θ3 and θ4, scan directions θ5 and θ6, ... in accordance with the same procedure. Besides, IQ signals obtained are successively saved in the Doppler signal storage circuit 326 (step S2 in FIG. 6).

Figure 8:
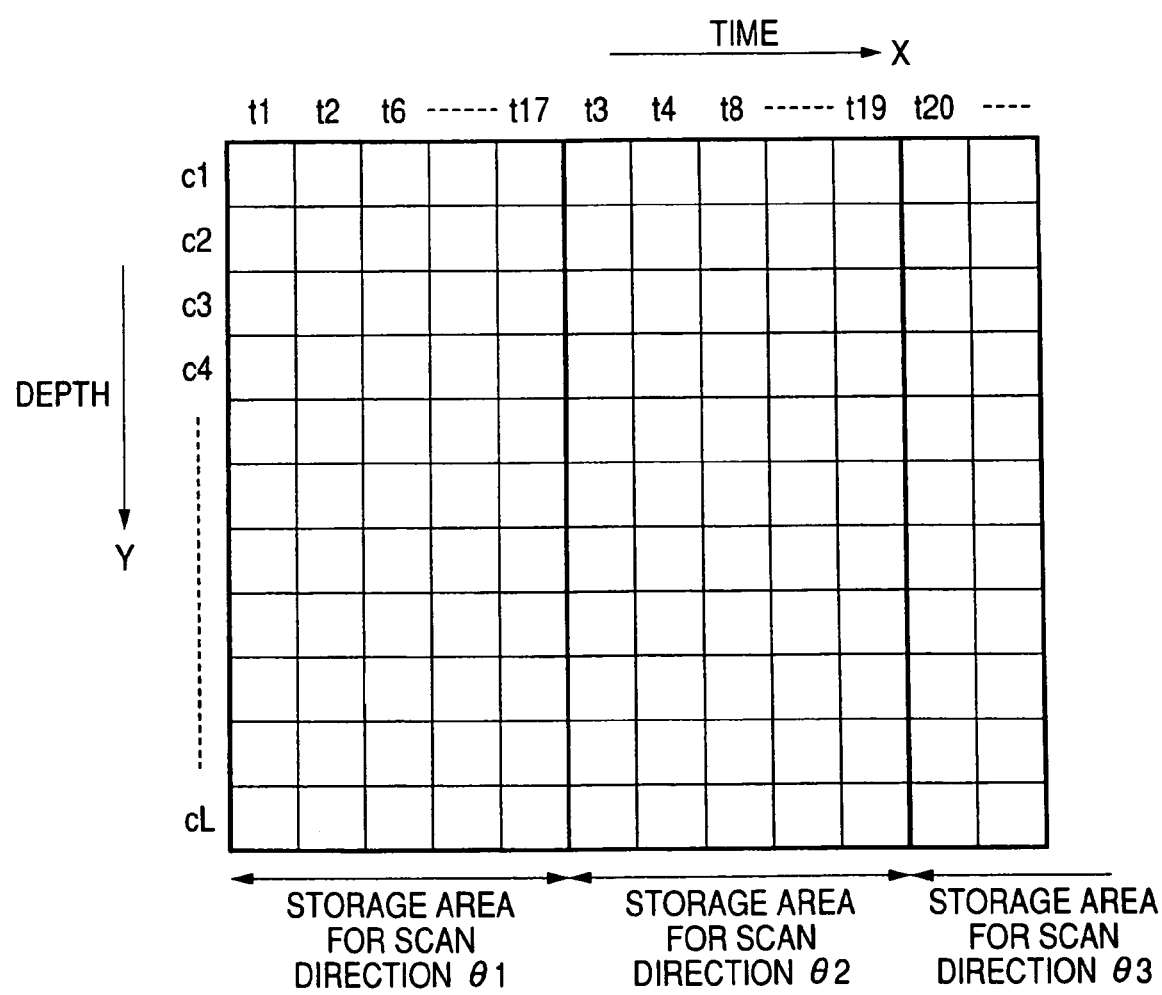
FIG. 8 is a diagram showing the structure of a Doppler signal storage circuit in the embodiment.

FIG. 8 shows the structure of the Doppler signal storage circuit 326. A row direction (X-direction) corresponds to the scan directions θ1 through θM or the transmission/reception times t1, t2, ..., while a column direction (Y-direction) corresponds to the depths of reflectors (distances between the reflectors and the ultrasonic probe 1). By way of example, the IQ signal obtained by the transmission/reception for the scan direction θ1 at the time t1 is saved in a column t1, and the IQ signals obtained by the transmissions/receptions for the scan direction θ1 at the times t2, t6, ..., and t17 are respectively saved in columns t2, t6, ..., and t17. Likewise, the IQ signals obtained by the transmissions/receptions for the scan direction θ2 at the transmission/reception times t3, t4, t8 ..., and t19 are respectively saved in columns t3, t4, t8 ..., and t19. Further, the IQ signals obtained in the scan directions θ3 through θM are similarly saved.

When the eight IQ signals obtained in the scan direction θ1 at the transmission/reception times t1, t2, t6 ..., and t17, and the eight IQ signals obtained in the scan direction θ2 at the transmission/reception times t3, t4, t8 ..., and t19 have been saved, the system control unit 7 reads out the IQ signals corresponding to a predetermined depth (for example, c1 in FIG. 8) among the eight IQ signals in the scan direction θ1, successively in the X-direction, so as to feed the read-out signals to the least squares filter 327.

Subsequently, the least squares filter 32-7 subjects the I components and Q components of the eight fed IQ signals, to curve fitting in the temporal direction (X-direction in FIG. 8), thereby to find clutter signals which are constituted by reflected waves from stationary reflectors such as tissues, tissue Doppler signals ascribable to the movements of the tissues, and so forth. Further, the least squares filter 327 subtracts the clutter signals from the IQ signals read out directly from the Doppler signal storage circuit 326, thereby to extract the IQ signals constituted by Doppler signals based on a blood flow (step S3 in FIG. 6).

Subsequently, the autocorrelation unit 328 selects the IQ signals U6 and U7 at the times t6 and t7 and those U11 and U12 at the times t11 and t12 as indicated in Equation (7), from among the IQ signals extracted in the least squares filter 327, so as to calculate the IQ signal Ux on the basis of Equation (8) (step S4 in FIG. 6).

Besides, the arithmetic unit 330 fed with the IQ signal Ux from the autocorrelation unit 328 calculates a phase difference Δϕx (namely, flow-velocity-value image data) on the basis of Equation (8), so as to save the calculated phase difference in the flow-velocity-value image data storage area of the image data storage unit 33 (step S5 in FIG. 6).

Further, the arithmetic unit 330 reads out the eight IQ signals in the scan direction θ1 as saved in the Doppler signal storage circuit 326, and it calculates a power value P and a variance value Var on the basis of these IQ signals (refer to Equation (9)). Besides, the arithmetic unit 330 saves the calculated power value P and variance value Var in the power-value image data storage area and variance-value image data storage area of the image data storage unit 33, respectively (step S6 in FIG. 6).

Subsequently, the least squares filter 327, autocorrelation unit 328, arithmetic unit 330 and image data storage unit 33 execute similar calculations for the decluttered IQ signals obtained from the IQ signals in the scan direction θ1 as correspond to all depths except the predetermined depth (for example, depths c2 through cL in FIG. 8), thereby to calculate flow velocity values, power values and variance values, which are saved. Further, the constituents 327, 328, 330 and 33 execute similar calculations for the eight IQ signals in the scan direction θ2 as saved in the Doppler signal storage circuit 326, thereby to calculate flow velocity values, power values and variance values at individual depths, which are saved.

When the B-mode image data and the color Doppler image data (namely, flow-velocity-value image data, power-value image data and variance-value image data) in the scan directions θ1 and θ2 have been generated and saved, interleave scans in the pair of scan directions, such as the scan directions θ3 and θ4 and those θ5 and θ6, are repeated by the same procedure, and B-mode image data and color Doppler image data obtained in the respective-pairs of scan directions are saved in the image data storage unit 33.

More specifically, the B-mode image data fed from the A/D converter 313 of the B-mode image data generation unit 31, and the flow-velocity-value image data, power-value image data and variance-value image data fed from the arithmetic unit 330 of the-Doppler image data generation unit 32 are successively saved in the image data storage unit 33, so as to generate two-dimensional B-mode image data, flow-velocity-value image data, power-value image data and variance-value image data (steps S2 through S7 in FIG. 6). Besides, these image data are fed to the DSC 41 of the display unit 4.

The DSC 41 of the display unit 4 saves the image data in the storage circuit once, and it thereafter affixes color information to the flow-velocity-value image data, power-value image data and variance-value image data. Besides, it synthesizes these image data and the B-mode image data, thereby to generate displaying image data. Further, it converts the displaying image data into a signal of standard television format, which is displayed on the color monitor 42 (step S8 in FIG. 6).

Next, the advantages of the least squares filter 327 employed in this embodiment will be described with reference to FIG. 9. The figure makes comparisons among a frequency characteristic (solid line) G1 in the case where the least squares filter 327 is applied to the IQ signals obtained by the unequally spaced transmissions/receptions of this embodiment, a frequency characteristic (broken line) G2 in the case where an MTI filter is applied to IQ signals in the equally spaced transmissions/receptions of the prior art, and a frequency characteristic (dot-and-dash line) G3 in the case where the MTI filter is applied to IQ signals in the unequally spaced transmissions/receptions of Patent Document 1. Herein, the axis of abscissas of the characteristic graph is normalized with the Nyquist frequency which is determined by the transmission/reception interval Tr of the equally spaced transmissions/receptions.

Figure 9:
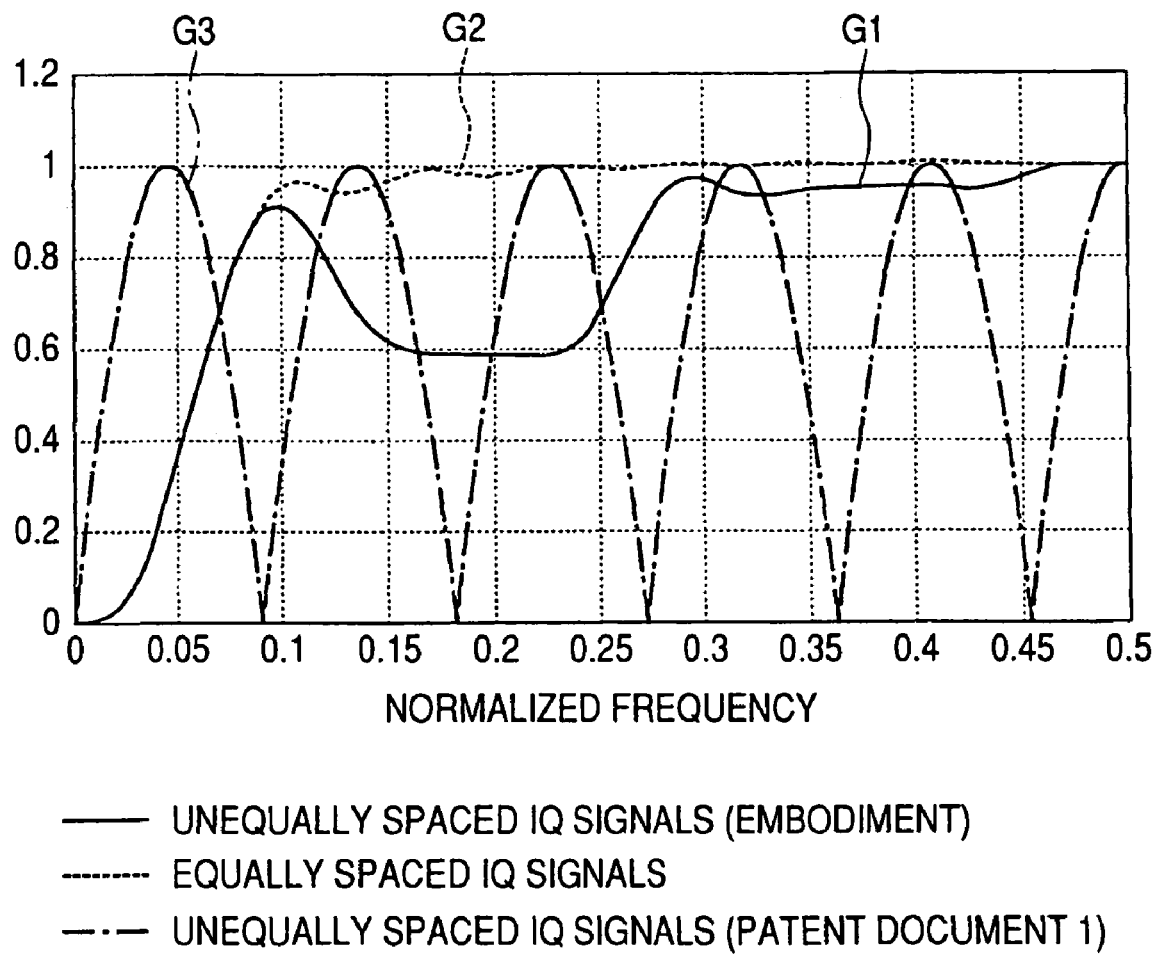
FIG. 9 is a graph showing the effect of a least squares filter in the embodiment.

As shown in FIG. 9, the frequency characteristic G3 in the method of Patent Document 1 as indicated by the dot-and-dash line undergoes a frequency (so-called "blind frequency") at which signals are cut off with a period being a frequency Δf (Δf=1/(T1+T2)) that is determined by the sum between the first transmission/reception interval T1 and second transmission/reception interval T2 stated before, and the IQ signals whose frequencies agree with the blind frequency fail to be detected. In contrast, the frequency characteristic G1 of this embodiment does not undergo any blind frequency in the frequency range of the characteristic graph, so that the IQ signals after the filtering process (that is, Doppler signals based on the blood flow) can be stably detected in a wide frequency band.

On the other hand, when compared with the frequency characteristic G2 in the prior-art equally spaced transmissions/receptions as indicated by the broken line, the frequency characteristic G1 of this embodiment contains frequency components which lack in flatness. The rugged levels of the frequency components, however, are allowable in the detection of the phase difference and the calculation of the power value as have already been described. Besides, since observation time periods for a predetermined direction are equal (17 Tr), the roll-off characteristics of the frequency characteristics as affect low-flow-velocity detectabilities become substantially equal. That is, according to this embodiment in which the least squares filter 327 is applied to the IQ signals of the unequally spaced transmissions/receptions, it is permitted to attain the frequency characteristic which is substantially equal to that in the case of applying the MTI filter to the IQ signals of the prior-art equally-spaced transmission/reception scheme.

(Modifications)

Next, modifications to the above embodiment will be described with reference to FIGS. 10A and 10B and FIGS. 11A and 11B. The characterizing feature of the modifications consists in that the unequally spaced transmission/reception and least squares filter method of the embodiment, and an autocorrelation method are applied to the prior-art interleave scan method.

Figure 10A:
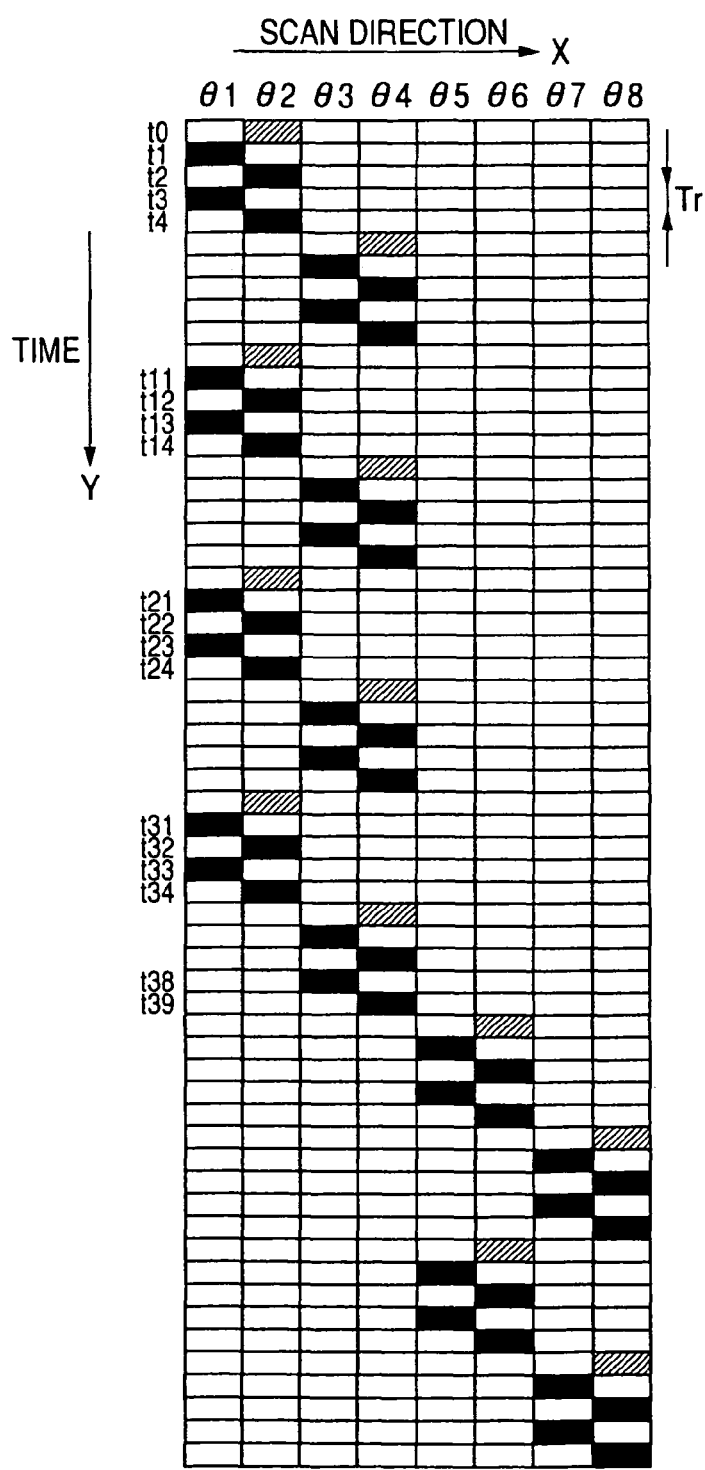
Figure 10B:
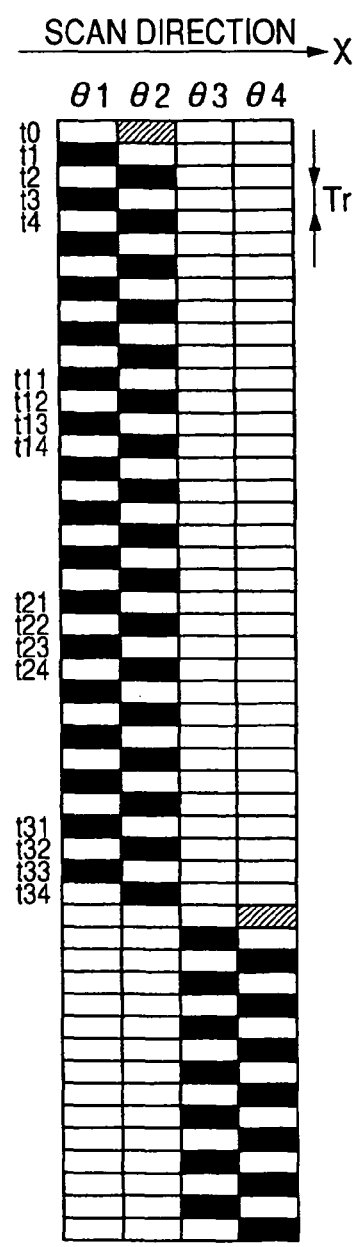
FIG. 10B is a diagram showing the sequence of transmissions/receptions which are performed by the prior-art interleave scan method.

FIG. 10A shows in a Y-direction, the sequence of transmissions/receptions which are performed for scan directions θ1 through θ8 in an X-direction by the modification, while FIG. 10B shows the sequence (Y-direction) of transmissions/receptions which are performed for the scan directions θ1 through θ4 (X-direction) by the prior-art. interleave method.

More specifically, in this modification, interleave scan is performed at transmission/reception intervals 2 Tr for the scan directions θ1 and θ2 at times t0 through t4, and similar interleave scan is subsequently performed for the scan directions θ3 and θ4 at times t5 through t9. Thereafter, interleave scans for the scan directions θ1 and θ2 are performed at times t10 through t14, times t20 through t24, and times t30 through t34, while interleave scans for the scan directions θ3 and θ4 are performed at times t15 through t19, times t25 through t29, and times t35 through t39. Besides, color Doppler image data are generated using eight reception signals during the observation time period of a period 33 Tr from the first transmission/reception time till the last transmission/reception time in each of the scan directions θ1 through θ8 (for example, from the time t1 till the time t33 for the scan direction θ1). Here, "Tr" denotes a transmission/reception interval in any of the scan directions.

In this case, the autocorrelation unit 328 executes autocorrelation processing by using IQ signals which are obtained from a predetermined position (depth) in the scan direction θ1 at the times t11 and t13 and the times t21 and t23. The arithmetic unit 330 calculates a flow velocity value and a variance value on the basis of the results of the autocorrelations, and it calculates a power value on the basis of respective IQ signals obtained from the predetermined position at the times t1, t3, t11, t13, t21, t23, t31 and t33. Subsequently, flow velocity values, variance values and power values are calculated by similar procedures for positions different from the predetermined position and for the scan directions θ2 through θ4.

On the other hand, FIG. 10B shows the prior-art interleave scan method which has the same observation time period 33 Tr as in FIG. 10A. Now, the betterment of a real-time responsivity in this modification will be explained by comparing FIG. 10A and FIG. 10B.

With the prior-art interleave scan method shown in FIG. 10B, a time period expended on the transmissions/receptions of ultrasounds for the two scan directions θ1 and θ2 is 35 Tr, whereas according to this modification in FIG. 10A, a time period expended on the transmissions/receptions for the four scan directions θ1 through θ4 becomes 40 Tr. Accordingly, the real-time responsivity in the case of generating color Doppler image data is bettered to be about 1.75 times higher, by this modification.

Incidentally, transmissions/receptions in the individual directions as are performed at the times t0, t5, t10, . . . in FIG. 10A and the times t0 and t35 in FIG. 10B are ones for relieving the influence of residual echoes (hereinbelow, termed "dummy transmissions/receptions"). In a case, for example, where the interleave scan of the scan directions θ1 and θ2 changes-over to that of the scan directions θ3 and θ4, the residual echo mixes into a reception signal immediately after the changeover, in a direction different from that of the other reception signal. Therefore, the dummy transmission/reception which does not contribute to calculations is performed in the case of the changeover between the interleave scans. That is, owing to the addition of the dummy transmissions/receptions, inputs to the least squares include the same residual echos. The same residual echos, i.e. DC signals can be eliminated by the least squares filter which fas a DC-cut characteristic. It is therefore permitted to eliminate calculation errors ascribable to the residual echoes.

Next, FIG. 11A shows the other modification to the foregoing embodiment, and it indicates scan directions θ1 through θ6 (X-direction) and a transmission/reception sequence (Y-direction) in this modification applying the interleave scan method. Besides, FIG. 11B indicates a transmission/reception sequence (Y-direction) in the prior art for the scan directions θ1 through θ3 (X-direction).

In the modification shown in FIG. 11A, unequally spaced transmissions/receptions for the scan direction θ1 are performed in an observation time period of times t0 through t15, and transmissions/receptions for the scan direction θ2 are performed at times (for example, at times t4, t5, t10 through t13, t18, and t19) at which the actual transmissions/receptions are not performed within the observation time period. Besides, for each of the scan directions, a flow velocity value, a power value and a variance value are calculated using five reception signals within the observation time period of 23 Tr. By way of example, the flow velocity value of the scan direction θ1 is calculated on the basis of an IQ signal obtained at the times t7 and t8, and an IQ signal obtained at the times t8 and t9.

With the prior-art transmission/reception method shown in FIG. 11B, a time period expended on the transmissions/receptions of ultrasounds for one scan direction is 16 Tr, whereas according to this modification in FIG. 11A, a time period expended on the transmissions/receptions for the two scan directions becomes 20 Tr. Accordingly, a real-time responsivity in the case of generating color Doppler image data is bettered to be about 1.6 times higher, by this modification.

By the way, in the two modifications, the transmission/reception interval and the observation time period in the IQ signals employed for the phase difference detection are the same as in the prior-art transmission/reception method, so that the low-flow-velocity detectabilities and high-flow-velocity detectabilities of the modifications become substantially the same as in the case of the prior-art transmission/reception method.

Figure 14:
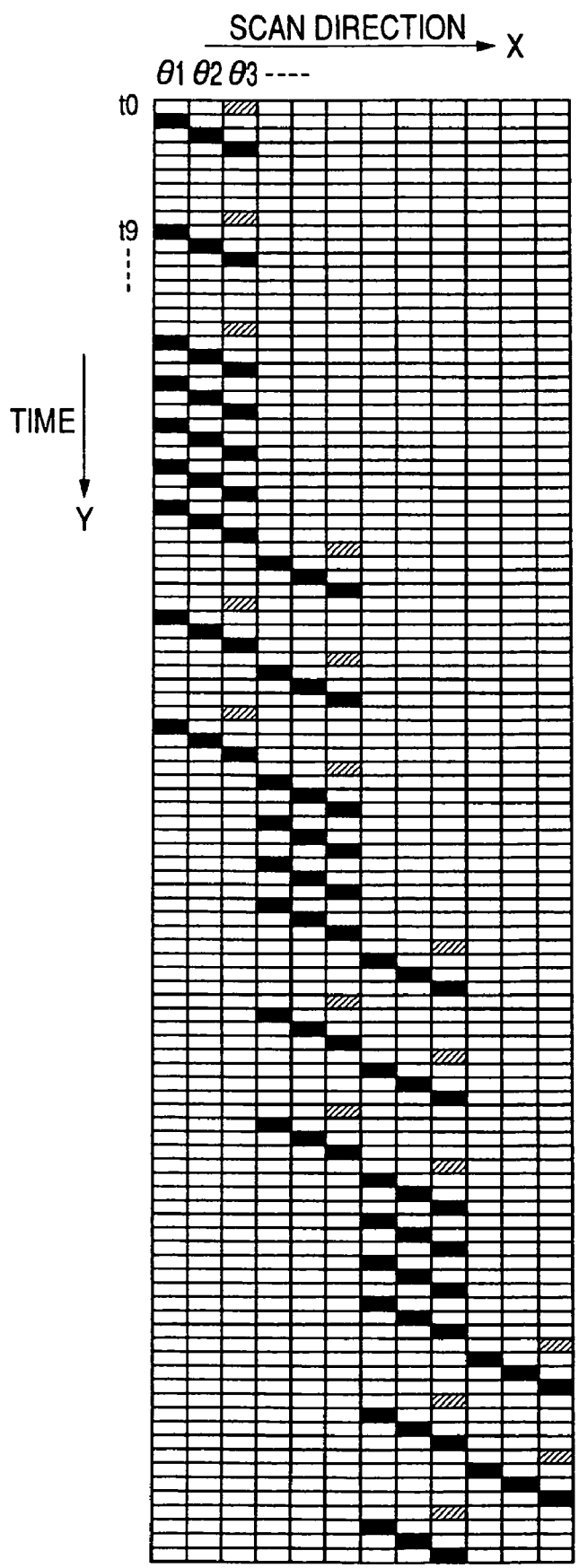
FIG. 14 is a diagram showing a scan method according to a third modification.

Next, a third modification to the foregoing embodiment will be described with reference to FIGS. 14 through 17. In this modification, scan is performed as shown in FIG. 14. In this figure, a horizontal direction represents the raster direction of ultrasounds, while a vertical direction represents the timings of the transmissions of the ultrasounds. Parts smeared in black indicate the timings of the transmissions whose ultrasounds are actually received, and hatched parts indicate dummy transmissions.

Figure 15A:
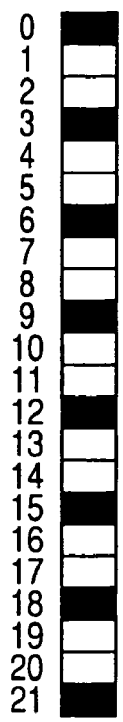
FIG. 15 is a diagram for comparing the scan method according to the third modification and the prior-art scan method.
Figure 15B:
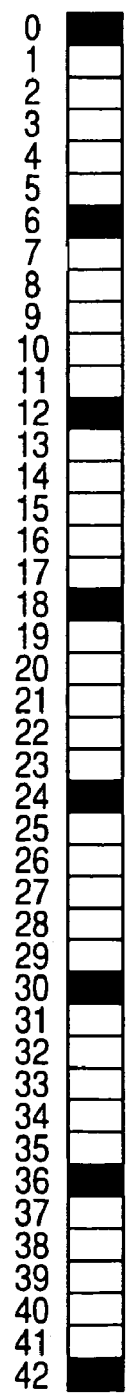
Figure 15C:
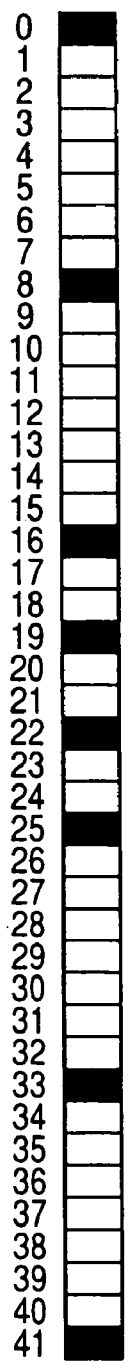

Part (c) in FIG. 15 shows only one raster extracted from within FIG. 14. Besides, part (a) in FIG. 15 shows equally spaced interleave scan of 3 stages for 8 data, the number of which is the same as at the part (c), and part (b) shows equally spaced interleave scan of 6 stages for 8 data. It is seen that the scan at the part (c) has substantially the same observation time period as at the part (b).

Figure 16:
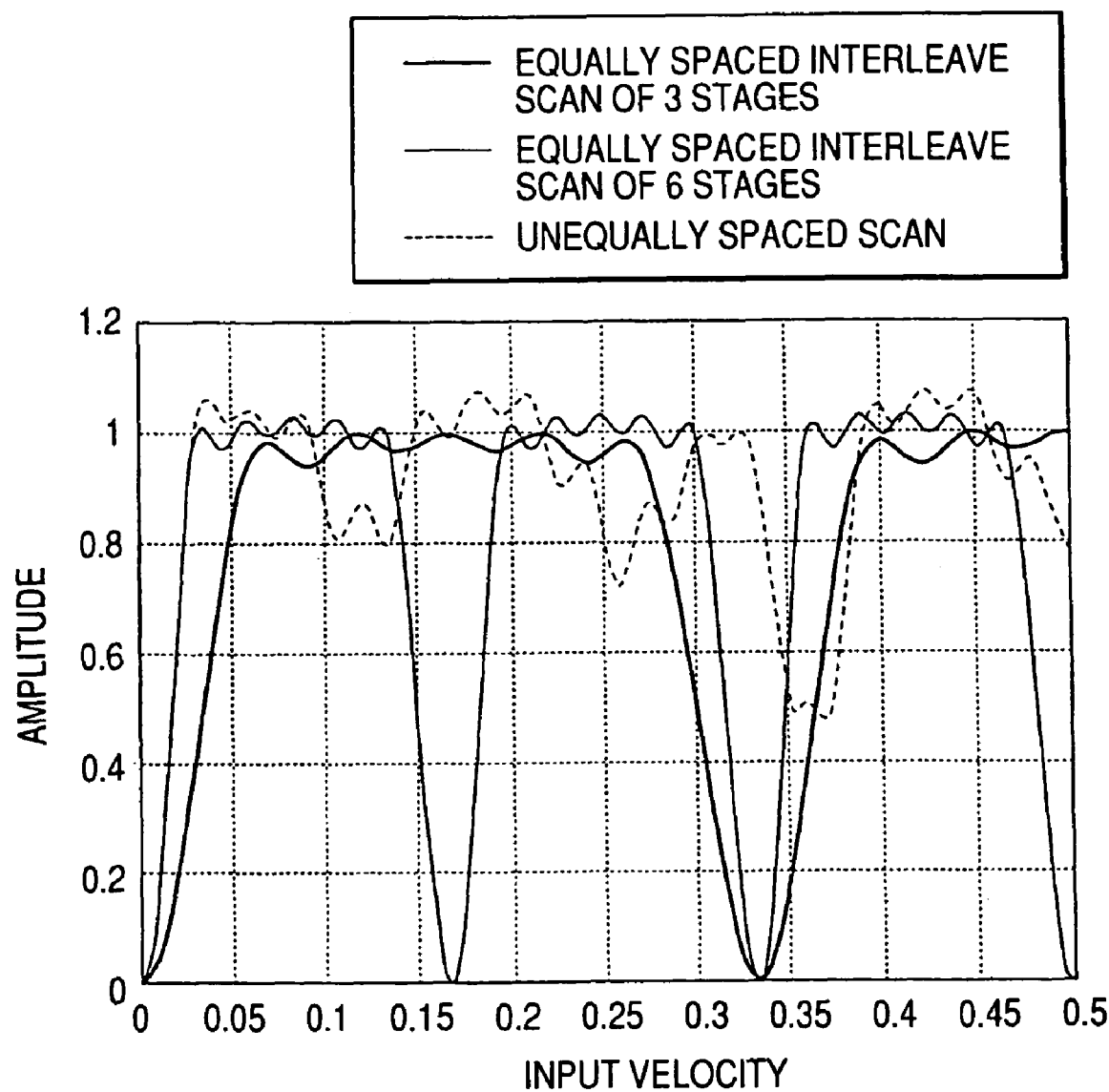
FIG. 16 is a graph showing the amplitude characteristic of the third modification after passage through a filter.

FIG. 16 shows amplitude characteristics versus input velocities as are exhibited after signals obtained by the scans at the parts (a), (b) and (c) in FIG. 15 have been passed through a filter which removes clutter signals by linear fitting. A velocity value of 0.5 corresponds to an aliasing frequency (Nyquist frequency) in the case where the transmission interval of the ultrasounds is set at 1 (one) It is seen that the equally spaced interleave scan of 6 stages as shown at the part (b), and the unequally spaced scan as shown at the part (c) have substantially equal suppressabilities in the transition region and rejection region of the filter at and below a frequency value of 0.03. This advantage comes from the fact that both the scans have substantially the same observation time period.

Figure 17:
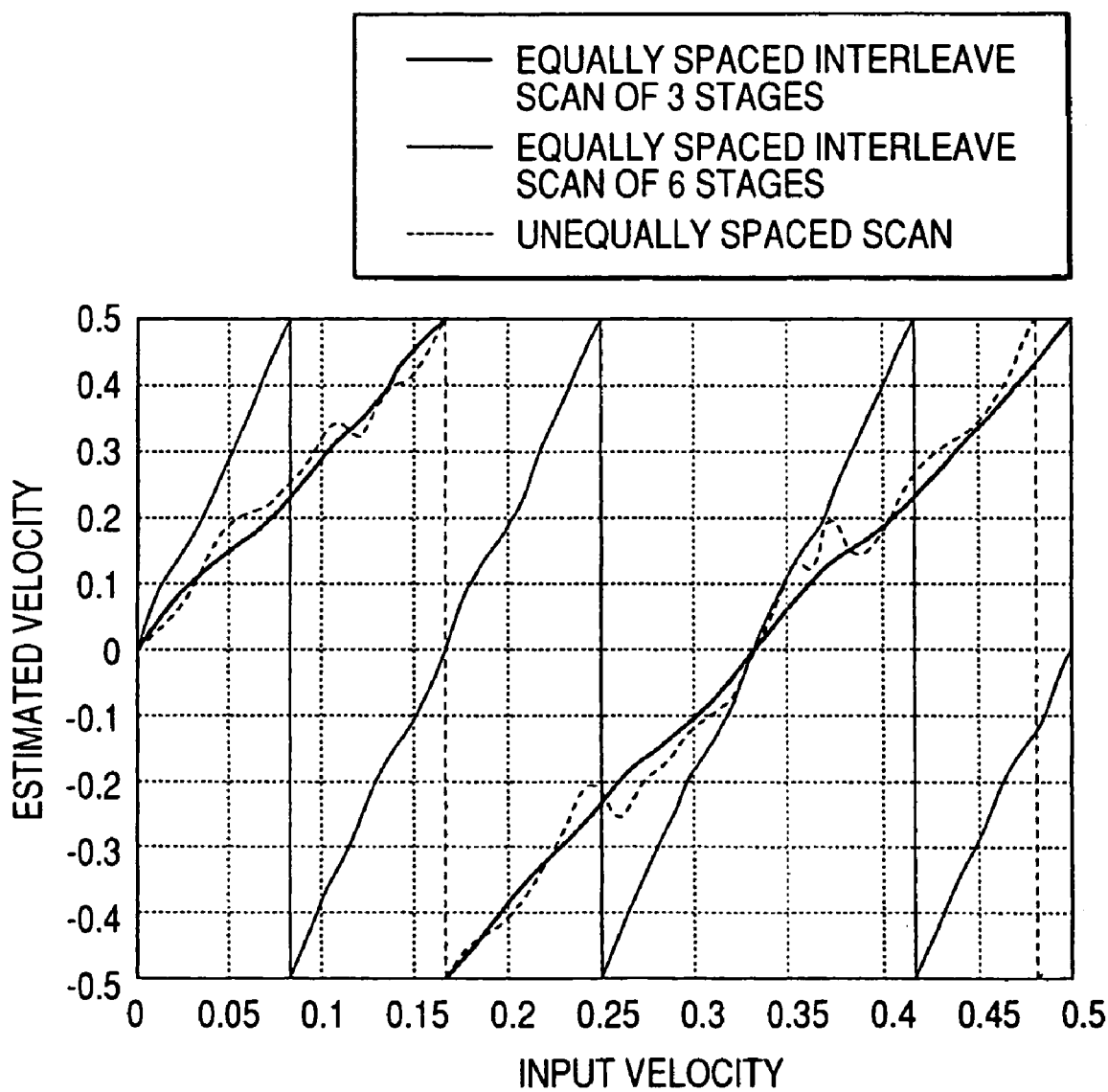
FIG. 17 is a graph showing the estimated velocity value of the third modification after the passage through the filter.

FIG. 17 is a graph showing estimated velocity values after the passage through the filter. By the way, in estimating the velocity values, central 6 data of the 8 data after the passage through the filter were used at the parts (a) and (b), and central 4 data after the passage through the filter were used at the part (c).

It is seen from FIGS. 16 and 17 that the equally spaced interleave scan of 3 stages exhibits a Nyquist frequency of 0.5/3=0.167, while the equally spaced interleave scan of 6 stages exhibits a Nyquist frequency of 0.5/6=0.083. These are natural results from the sampling theorem. In the equally spaced interleave scan of 3 stages, a frequency value of 0.333 forms a blind frequency (at which an amplitude becomes zero), while in the equally spaced interleave scan of 6 stages, frequency values of 0.167, 0.333 and 0.5 form blind frequencies.

In the unequally spaced scan shown at the part (c) in FIG. 15, however, any blind frequency does not exist except for DC as seen from the amplitude characteristic in FIG. 16. As seen from the part (c) in FIG. 15, the endmost and second-endmost sampling points do not lie at positions which are integral times the extraction intervals 3 of the central 4 data. This is the reason why the blind frequency does not exist except for the DC in the amplitude characteristic. On the other hand, regarding the estimated velocity, it is seen from FIG. 17 that the unequally spaced scan shown at the part (c) in FIG. 15 exhibits the same aliasing velocity as in the equally spaced interleave scan of 3 stages shown at the part (a). This is because the velocity estimation uses only the central data of the extraction intervals 3.

According to the embodiment and modifications described above, ultrasonic transmissions/receptions at unequal intervals or in unequally spaced fashion are performed for the predetermined direction of a patient, and a filter based on the least squares method is applied to reception signals obtained, whereby IQ signals subjected to a filtering process as exhibit a frequency characteristic having a smaller number of blind frequencies can be detected.

Besides, among IQ signals obtained by the unequally spaced transmissions/receptions, IQ signals subjected to the filtering process as obtained in adjacency at a short transmission/reception interval has their phase difference detected, whereby a high-flow-velocity detectability can be enhanced.

Further, unequally spaced transmissions/receptions for a direction different from the predetermined direction of the patient are performed at long transmission/reception intervals among the plurality of unequally set transmission/reception intervals, whereby the transmissions/receptions for the plurality of directions can be concurrently performed, and a real-time responsivity in the display of color Doppler image data can be bettered.

That is, in the embodiment and modifications, the above advantages can be simultaneously attained, so that a color Doppler image of superior low-flow-velocity detectability and high-flow-velocity detectability can be obtained without degrading the real-time responsivity.

Figures 12A, 12B:
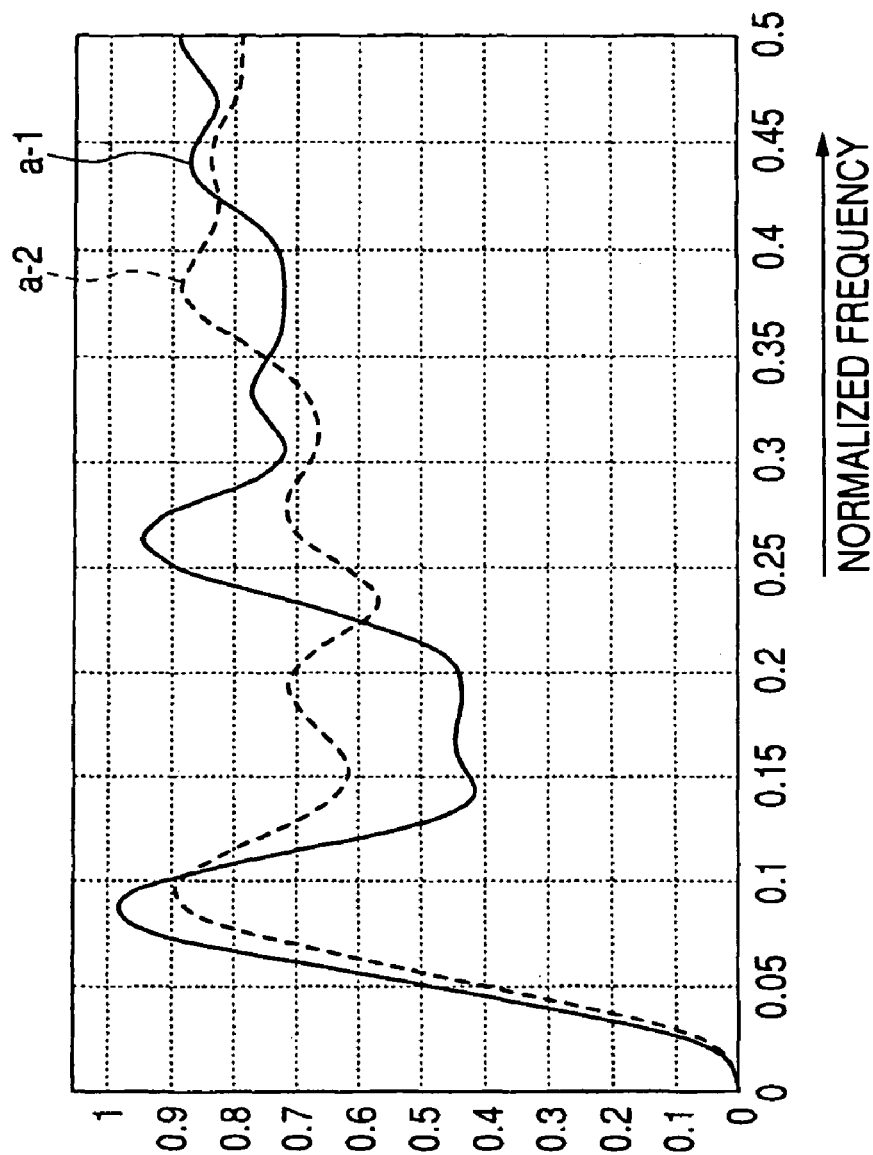

Although the embodiments of the present invention have been described above, the invention is not restricted to the embodiments, but it can be altered and performed. By way of example, the settings of unequally spaced transmission/reception times are not restricted to the methods indicated in the foregoing embodiment and modifications. FIG. 12A shows two sorts of unequally spaced transmissions/receptions which have been extracted from within 18 transmission/reception times set at equal intervals Tr. Part a-1 corresponds to a case where the transmissions/receptions are uniformly extracted, and part a-2 corresponds to a case where the transmissions/receptions are extracted so as to be densified in a central region. On the other hand, FIG. 12B shows frequency characteristics exhibited when a least squares filter was applied to reception signals (IQ signals) obtained by the two sorts of unequally spaced transmissions/receptions. As seen from these results, the more excellent frequency characteristic can be attained in the case of setting the unequally spaced transmissions/receptions densified in the central region.

Meanwhile, in the invention, a least squares filter may well be applied to a flow-velocity-value calculation method employing an autocorrelation process. In the calculation of a flow velocity value based on the autocorrelation process as described in the foregoing embodiment, the restrictions of aliasing are inevitable. As a method for alleviating the problem of the aliasing, a flow-velocity-value estimation method employing a cross-correlation process has been proposed in, for example, JP-A-2-326172. In the flow-velocity-value estimation method employing the cross-correlation process, ultrasounds are transmitted/received in a predetermined direction a plurality of times, and cross-correlation calculations are executed in the transmission/reception direction for two reception signals obtained in adjacency in a temporal direction. Besides, a flow velocity value is found on the basis of a positional shift for which the largest correlative value is obtained.

In, for example, the transmission/reception method shown in FIG. 7, clutter signals are excluded from reception signals obtained by transmissions/receptions at times t6 and t7, and Doppler signals U6 and U7 obtained are subjected to cross-correlation calculations in a transmission/reception direction, in accordance with Equation (10) below. Besides, a flow velocity value "V" is obtained in such a way that a positional shift "Δz=ZO" which maximizes a correlative value "R(z, Δz)" is substituted into V=ZO/Tr. In the equation, "U*" represents the complex conjugate of the reception signal "U".

$$R(z, \Delta z) = \sum_{k=-Ma}^{Ma} u_6^*(z+k) u_7(z+k+\Delta z) \tag{10}$$

The clutter signals in this case are removed in such a way that, as in the case of the foregoing embodiment, a filtering process is executed for the reception signals of predetermined depth obtained by the plurality of times of transmissions/receptions for the predetermined transmission/reception direction. Besides, in a blood flow measurement based on the cross-correlation process, the problem of a blind frequency which appears in case of performing unequally spaced transmissions/receptions is alleviated by applying the least squares filter.

Next, in a case where adaptive phase corrections are made for unequally spaced reception signals, the least squares filter mentioned in the embodiment may well be applied. Such an adaptive phase correction method is disclosed in JP-A-10-99333. FIG. 13 shows the adaptive phase correction method for a string of unequally spaced reception signals. As indicated in Equation (11) below, the phase differences $\phi_1$ through $\phi_7$ between the reception signals obtained in adjacency within the string of reception signals $y_n$ (n=1 through 8) are first detected. Subsequently, phases $\Phi_n$ corresponding to the reception signals $y_n$ are evaluated by adding the phase differences $\phi_1$ through $\phi_{n-1}$, and a string of corrected reception signals $yy_n$ (n=1 through 7) are calculated on the basis of the phases $\Phi_n$.

$$\Phi_1 = 0 \tag{11}$$

$$\Phi_n = \sum_{k=1}^{n-1} \Phi_k \quad (n \geq 2)$$

$$yy_n = y_n \exp(-j\Phi_n)$$

Besides, Doppler signals $U_n$ (n=1 through 8) for a blood flow can be obtained in such a way that the reception signal string $yy_n$ is multiplied by an unequally spaced filter matrix [W].

Meanwhile, the filter matrix [W] employed in the embodiment is one of solutions based on the least squares method. The employed method is not restrictive, but it is also allowed to employ another method, for example, a method utilizing singular-value decomposition, or a method utilizing a orthonormal expansion matrix.

Besides, the embodiment of the invention has been described on the ultrasonic diagnostic equipment which includes the ultrasonic probe having the piezoelectric transducers arrayed unidimensionally, and the reception unit of analog scheme, but the invention is not restricted to the embodiment. The invention may well be applied to, for example, an ultrasonic diagnostic equipment which copes with an ultrasonic probe including piezoelectric transducers of two-dimensional array, or an ultrasonic diagnostic equipment which includes a reception unit of digital scheme.

Further, in the embodiment, the orthogonal phase detection has been executed for the reception signals obtained by the unequally spaced transmissions/receptions, and the filtering process and the autocorrelation process have been executed for the IQ signals obtained, but the invention is not restricted to this method.

What is claimed is:

1. An ultrasonic diagnostic equipment comprising:
an ultrasonic probe which includes piezoelectric transducers for transmitting/receiving ultrasonic pulses to and from a mobile object within a patient;
a transmission/reception device configured to drive the piezoelectric transducers so as to transmit the ultrasonic pulses at unequal intervals, including a first interval and a second interval longer than the first interval, in a predetermined scan direction during transmission, and such that the ultrasonic pulses transmitted at the first interval are adjacent ultrasonic transmissions, and to receive the ultrasounds from the predetermined scan direction to obtain information for one frame;
a Doppler signal detection device configured to execute a filtering process for a plurality of reception signals obtained in time series at the unequal intervals from a predetermined position within the body by said transmission/reception device, thereby to detect Doppler signals based on the mobile object;
a velocity calculation device configured to select Doppler signals adjacent to each other at the first interval from among the plurality of Doppler signals obtained at the unequal intervals by said Doppler signal detection device, and which calculates a velocity of the mobile object on the basis of the selected Doppler signals; and
an image data generation device configured to generate velocity image data on the basis of the velocity of the mobile object as calculated by said velocity calculation device.

2. An ultrasonic diagnostic equipment comprising:
an ultrasonic probe which includes piezoelectric transducers for transmitting/receiving ultrasonic pulses to and from a mobile object within a body;
a transmission/reception device configured to drive the piezoelectric transducers so as to transmit the ultrasonic pulses at unequal intervals having a first interval and a second interval longer than the first interval, in a first scan direction and a second scan direction, respectively, during transmission, and such that the ultrasonic pulses transmitted at the first interval are adjacent ultrasound transmissions, and to receive the ultrasounds from the scan directions to obtain information for one frame;
a Doppler signal detection device configured to select a filtering process for a plurality of reception signals obtained in time series at the unequal intervals from a predetermined position within the body by said transmission/reception device, thereby to detect Doppler signals based on the mobile object;
a velocity calculation device configured to select Doppler signals adjacent to each other at the first interval, from among the plurality of Doppler signals obtained by said Doppler signal detection device, and which calculates a velocity of the mobile object on the basis of the selected Doppler signals;
a scan control device configured to perform ultrasonic scans while the first scan direction and the second scan direction are being successively altered;
an image data generation device configured to generate velocity image data on the basis of the velocities of the mobile object as calculated by said velocity calculation device, in the ultrasonic transmissions at the unequal intervals in the respective scan directions of the ultrasonic scans; and
a display device configured to display the generated image data;
wherein the ultrasonic transmission/reception in the second scan direction are performed at the second interval of the ultrasonic transmission/reception in the first scan direction.

3. An ultrasonic diagnostic equipment according to claim 1, wherein said Doppler signal detection device executes the process based on fitting, for the plurality of reception signals obtained in time series, thereby to extract reception signals from either of a stationary object and a mobile object of low moving velocity, and it subtracts the reception signals after the process, from the reception signals before the process, thereby to detect the Doppler signals based on the mobile object.

4. An ultrasonic diagnostic equipment according to claim 3, wherein the process based on the fitting is a process based on polynomial least-squares fitting.

5. An ultrasonic diagnostic equipment according to claim 1, wherein said Doppler signal detection device removes reception signals from either of a stationary object and a mobile object of low moving velocity by employing a matrix which utilizes one member selected from the group consisting of a least squares method, singular-value decomposition and orthonormal expansion.

6. An ultrasonic diagnostic equipment according to claim 1, wherein said velocity calculation device selects the Doppler signals adjacent at a least interval, from among the Doppler signals at the unequal intervals, and it calculates the velocity of the mobile object on the basis of the selected Doppler signals.

7. An ultrasonic diagnostic equipment according to claim 1, wherein said velocity calculation device calculates the velocity of the mobile object by detecting a phase difference between the Doppler signals which are adjacent at the first interval.

8. An ultrasonic diagnostic equipment according to claim 7, wherein said velocity calculation device selects a plurality of pairs of Doppler signals adjacent at the first interval, from among the Doppler signals at the unequal intervals, and it calculates the velocity of the mobile object by taking a sum-square mean value of phase differences in the respective Doppler signal pairs.

9. An ultrasonic diagnostic equipment according to claim 8, wherein said transmission/reception device lowers a frequency in the ultrasonic transmission/reception adjacent at the first interval, at an initial stage and a terminal stage of the ultrasonic transmission/reception at the unequal intervals.

10. An ultrasonic diagnostic equipment according to claim 1, wherein said velocity calculation device calculates the velocity of the mobile object by executing a cross-correlation process in the ultrasonic transmission direction, for the Doppler signals adjacent at the first interval.

11. An ultrasonic diagnostic equipment according to claim 1, further comprising a power calculation device configured to calculate power on the basis of signal intensities of the plurality of Doppler signals detected at the unequal intervals by said Doppler signal detection device.

12. An ultrasonic diagnostic equipment according to claim 11, wherein said power calculation device calculates the power by using all of the plurality of Doppler signals detected at the unequal intervals by said Doppler signal detection device.

13. An ultrasonic diagnostic equipment according to claim 11, wherein said image data generation device generates power image data on the basis of the power calculated by said power calculation device, in addition to the generation of the velocity image data.

14. An ultrasonic diagnostic equipment according to claim 2, wherein said scan control device sets the second scan direction to be adjacent to the first scan direction.

15. A method of controlling an ultrasonic diagnostic equipment, comprising:
- a transmission/reception step of driving piezoelectric transducers of an ultrasonic probe which includes the piezoelectric transducers for transmitting/receiving ultrasonic pulses to and from a mobile object within a body, so as to transmit the ultrasonic pulses at unequal intervals, having a first interval and a second interval longer than the first interval, in a predetermined scan direction during transmission, and such that the ultrasonic pulses transmitted at the first interval are adjacent ultrasound transmissions, and to receive the ultrasonic pulses from the predetermined scan direction to obtain information for one frame;
- a Doppler signal detection step of executing a filtering process for a plurality of reception signals obtained in time series at the unequal intervals from a predetermined position within the body by said transmission/reception step, thereby to detect Doppler signals based on the mobile object;
- a velocity calculation step of selecting Doppler signals adjacent to each other at the first interval, from among the plurality of Doppler signals obtained by said Doppler signal detection step, and then calculating a velocity of the mobile object on the basis of the selected Doppler signals; and
- an image data generation step of generating velocity image data on the basis of the velocity of the mobile object as calculated by said velocity calculation step.

16. A method of controlling an ultrasonic diagnostic equipment, comprising:
- a transmission/reception step of driving piezoelectric transducers of an ultrasonic probe which includes the piezoelectric transducers for transmitting/receiving ultrasonic pulses to and from a mobile object within a body, so as to transmit the ultrasonic pulses at unequal intervals having a first interval and a second interval longer than the first interval, in a first scan direction and a second scan direction, respectively, during transmission, and such that the ultrasonic pulses transmitted at the first interval are adjacent ultrasound transmissions, and to receive the ultrasonic pulses from the first scan direction and the second scan direction to obtain information for one frame;
- a Doppler signal detection step of executing a filtering process for a plurality of reception signals obtained in time series at the unequal intervals from a predetermined position within the body by said transmission/reception step, thereby to detect Doppler signals based on the mobile object;
- a velocity calculation step of selecting Doppler signals adjacent to each other at the first interval, from among the plurality of Doppler signals obtained by said Doppler signal detection step, and then calculating a velocity of the mobile object on the basis of the selected Doppler signals;
- a scan control step of performing ultrasonic scans while the first scan direction and the second scan direction are being successively altered;
- an image data generation step of generating velocity image data on the basis of the velocities of the mobile object as calculated by said velocity calculation step, in the ultrasonic transmissions at the unequal intervals in the respective scan directions of the ultrasonic scans; and
- a display step of displaying the generated image data;
- wherein the ultrasonic transmission/reception in the second scan direction are performed at the second interval of the ultrasonic transmission/reception in the first scan direction.

* * * * *